United States Patent [19]
Adachi et al.

[11] Patent Number: 5,588,254
[45] Date of Patent: Dec. 31, 1996

[54] PLANT CULTIVATION METHOD

[75] Inventors: Takashi Adachi; Takafumi Ishii; Hidemasa Hidaka, all of Kanagawa, Japan

[73] Assignee: Meiji Seika Kaisha, Ltd., Tokyo, Japan

[21] Appl. No.: 571,003

[22] Filed: Aug. 22, 1990

Related U.S. Application Data

[63] Continuation of Ser. No. 109,374, Oct. 19, 1987, abandoned.

[30] Foreign Application Priority Data

Oct. 17, 1986 [JP] Japan ................... 61-245400
Mar. 3, 1987 [JP] Japan ................... 62-48385

[51] Int. Cl.$^6$ ................ A01H 1/00; A01N 63/00; A01N 65/00
[52] U.S. Cl. ................ 47/57.6; 47/58; 504/100; 504/121; 427/4
[58] Field of Search ................ 47/58, 57.6; 71/6; 435/73, 240.4; 427/4; 111/6; 504/100, 121

[56] References Cited

U.S. PATENT DOCUMENTS

| | | | |
|---|---|---|---|
| 4,226,855 | 10/1980 | Shigematsu | 424/177 |
| 4,617,049 | 10/1986 | Lengyel | 71/88 |
| 4,918,009 | 4/1990 | Nilsson | 435/73 |

FOREIGN PATENT DOCUMENTS

| | | |
|---|---|---|
| 0179324 | 4/1986 | European Pat. Off. . |
| 8500002 | 1/1985 | WIPO . |

OTHER PUBLICATIONS

Albertsheim et al. (1985) Scientific American 253(3) pp. 58–64.
Stanek et al (1983) Folia Microbiol 28, 91–99.
Lasik et al (1979) Folia Microbiol 24, 262–268.
Shelukhina et al (1984) Derwent Abstract No. C86–023164.

*Primary Examiner*—Gary Benzion
*Attorney, Agent, or Firm*— Sughrue, Mion, Zinn, Macpeak & Seas

[57] ABSTRACT

A method for cultivating plants comprises using a plant growth accelerating oligosaccharide obtained by decomposing a polysaccharide.

6 Claims, No Drawings

PLANT CULTIVATION METHOD

This is a Continuation of application Ser. No. 07/109,374 filed Oct. 19, 1987, now abandoned.

FIELD OF THE INVENTION

This invention relates to a method of cultivating plants capable of efficiently producing agricultural products by accelerating the growth of plants by applying to the plants or the solid the decomposition products of a polysaccharide which is specifically selected from the view point of having a growth accelerating action for the plants or an oligosaccharide which is the main component of the aforesaid decomposition products.

BACKGROUND TO THE INVENTION

It is an important subject for producing agricultral products by accelerating the growth of agricultural plants to increase the yield per unit area and further to increase the cultivating number of times. As growth accelerating materials for plants, plant hormones such as gibberellin and auxin are reported, but such a plant hormone gives various actions on plants; that is, some actions of the plant hormone are useful for the plant but other actions are, sometimes, harmful for the plant, and hence the practical use of such a plant hormone is limited to a specific case.

On the other hand, recently it has been reported that an oligosaccharide obtained by the decomposition of a polysaccharide. constituting the cell walls of plant has an important role as a material for controlling the plant host defence and the differentiation of the plant itself.

For example, it is reported that oligogalacturonic acid, when applied to soybean, has an action of accelerating the synthesis of a certain kind of antibacterial material (Phyloalexin) to increase the resistance of the soybean to disease germs and also an oligosaccharide (xyloglucan) prepared from the cell wall of a maple tree has an effect of, on the contrary, restraining the growth acceleration action of auxin to the seedlings of peas.

As described above, the action of an oligosaccharide is rather different from a plant hormone.

SUMMARY OF THE INVENTION

The object of this invention is to increase the efficiency of the production of agricultural products by applying to the production of agricultural products a specific oligosaccharide having an action of accelerating the growth of plants selected from various oligosaccharides.

As the result of various investigations on oligosaccharides having an action of accelerating the growth of plants for attaining the aforesaid object of this invention, the inventors have discovered a new fact that some of the decomposition products obtained by decomposing polysaccharides with an acid or an enzyme or oligosaccharides which are the main components of the decomposition products have an action of accelerating the growth of roots stalks, and leaves of plants and have succeeded in accomplishing the present invention based on that discovery.

According to this invention, there is provided a method for cultivating a plant, which comprises using an oligosaccharide having an action of accelerating the growth of the plant at the cultivation of the plant.

DETAILED DESCRIPTION OF THE INVENTION

The polysaccharides which may be used as a raw material for the oligosaccharide in this invention include various polysaccharides produced by microorganisms (e.g., rooting zone rhizobacteria), alginic acid, xylan, cell wall polysaccharides of plants, polygalacturonic acid, pectin, glucomannan, agarose, cellulose, inulin, mannan, fucoidin, gum arabic, polyethylene glycol alginic acid, carrageenan, etc. It is a new fact, which has never been known, that the decomposition products of such polysaccharides or oligosaccharides which are the main components of these decomposition products have an action of accelerating the growth of plants.

As plants suitable for use in the method of this invention, there are green plants such as Kaiware Daikon (literally, cotyledon radish, artificially-grown radish having white stalks and cotyledon), stone parsley (Cryptotaenia japonica Hassk) Chinese cabbage, lettuce, spinach, radish, potato, taro, etc., cereals such as rice plant, wheat, corn plant, etc., and other agricultural products such as petals, fruits, etc.

The oligosaccharide having an action of accelerating the growth of plants in this invention means a decomposition product of the above-described polysaccharide or a natural product containing the same with an acid or an enzyme, or the oligosaccharide which is the main component of the decomposition product and is defined as a material having an action of accelerating the growth of plants. The oligosaccharide in this invention is, for example, defined for each substance as follows.

(1) Alginic Acid Oligosaccharide:

This oligosaccharide is an oligosaccharide composition obtained by decomposing alginic acid, sodium alginate, algae containing alginic acid, such as sea algae (Laminaria), etc., a microorganism-originated polysaccharide, etc., with an enzyme such as alginic acid lyase, etc., or by hydrolyzing the above-described material with an acid such as hydrochloric acid, etc., and the main saccharide components constituting the oligosaccharides are guluronic acid and/or mannuronic acid. The composition of the alginic acid oligosaccharide and comprises guluronic acid only or mannuronic acid only having a polymerization degree of from 2 to 20, or the oligosaccharides constituted by a combination of the guluronic acid and the mannuronic acid, a composition composed of guluronic acid and mannuronic acid, or further a composition obtained by heating the aforesaid composition for 15 to 180 minutes at a temperature of from 100° to 130° C. at pH of from 1 to 3.

The composition described above is, for example, prepared as follows.

As alginic acid for use as the raw material, any alginic acid-containing raw materials, e.g., commercially available alginic acid or sodium alginate; algae containing alginic acid, such as Laminaria, Ecklomia cava, Lessonia, Durvilla, etc.; alginic acid-like polysaccharide produced by microorganisms such as Pseudomonas, etc., can be utilized.

In the description, unless otherwise indicated, all parts and percents are by weight.

As a means for decomposing the alginic acid, a method of decomposing with an acid such as hydrochloric acid, sulfuric acid, etc., and a method of decomposing with an enzyme such as alginic acid lyase, etc., can be applied. In the case of decomposing the alginic acid with an acid, the alginic acid oligosaccharide can be prepared, for example, by adding 100 parts of water to 5 parts of sodium alginate to dissolve alginic acid, adding thereto 3 parts of concentrated hydrochloric acid, after hydrolyzing the alginic acid for 2 to 4 hours at 90° to 100° C., filtering the reaction mixture, nuetralizing the filtrate thus obtained with sodium hydroxide, and concentrating the neutralized product. In the case of decomposing the alginic acid with alginic acid lyase, the alginic acid oligosaccharide can be prepared, for example, by adding 100 parts of water to 5 parts of sodium alginate to dissolve alginic acid, adjusting the pH of the solution to the optimum value for the action of an enzyme, adding thereto an enzyme at from 100 to 4,000 units per gram of sodium alginate, and reacting both components for 24 to 48 hours at the optimum temperature for the action of the enzyme.

When an alimentary canal enzyme of abalone (Abalone Acetone Powder, trade name, made by Merck & Co., Inc.) is used as the alginic acid lyase, the optimum pH for the action of the enzyme is from 7 to 8 and the optimum temperature is from 20° to 35° C.

The enzyme activity of alginic acid lyase capable of increasing the absorbance of the system at 230 nm by 0.01 in 30 minutes when the enzyme was allowed to act on an aqueous solution of 0.2% sodium alginate at 30° C. add pH 7.0, is defined as 1 unit.

In the case of obtaining an oligosaccharide directly from algae, the alginic acid oligosaccharide can be directly produced, for example, from sea tangle (Laminaria) by adding 1,300 parts of water to 40 parts of dry sea tangle, after adjusting the pH of the mixture to 11, pulverizing the sea tangle by means of a homogenizer, heating the mixture to 60° C. for 3 hours, after adjusting the pH thereof to 5.5, adding cellulase (Meicelase, trade name, made by Meiji Seika Kaisha, Ltd.) in an amount of 0.5% to the solid content, performing the reaction for 20 hours at 40° C., adjusting the pH of the reaction mixture to 7.0, adding thereto alginic acid lyase at 1,000 units per gram of the solid components, and then performing the reaction for 48 hours at 30° C.

The alginic acid oligosaccharide thus obtained is composed mainly of mannuronic acid and guluronic acid and is any one of the compositions comprising guluronic acid only or mannuronic acid only having a polymerization degree of from 2 to 20, or the oligosaccharide is composed of a combination of the guluronic acid and the mannuronic acid, or a mixture of the guluronic acid and the mannutonic acid.

The content of the alginic acid oligosaccharide in the decomposition products obtained as described above depends upon the kind of the raw material used but in the case of preparing the decomposition products, for example, by an enzyme decomposition of sodium alginate as the raw material, the content of the alginic acid oligosaccharide amounts to from 40 to 100% of the solid components in the products. Also, in the case of using a sea weed such as sea tangle as the raw material, the content amounts to from 10 to 20% of the solid components.

When the alginic acid oligosaccharide thus obtained is applied to plants by coating seeds with it, by adding it to the soil or spraying it onto the surfaces of leaves as 0.25 to 0.00025% aqueous solutions thereof, or by adding it to a liquid fertilizer for hydroponics, growth of the root or the above ground portions of the plants is accelerated, resulting in improved yield of the agricultural products. In this case, it has further been clarified that the aforesaid action is further increased by heat-treating the composition obtained as described above at a temperature of from 100° to 120° C. and at a pH of from 1 to 3, and preferably from 2.0 to 3.0 for 15 to 180 minutes. In addition, undecomposed alginic acid or sodium alginate did not give any action of accelerating the growth of plants, as shown in Example 1 described hereinafter.

(2) Xylooligosaccharide:

Xylooligosaccharide is a decomposition product (or an oligosaccharide of its main component) formed by decomposing $\beta$-1,3-xylan, $\beta$-1,4-xylan, or the hemicellulose components of vegetables or plants containing the xylans, such as corn cobs, rice straws, wood, etc., or algae belonging to red algae (Rhodophyceae) or green algae (Chlorophyceae) such as Rhodymenia palmata, Caulerpa racemosa, etc., with an acid such as hydrochloric acid, etc., or an enzyme such as xylanase, etc. The saccharide contituting the oligosaccharide is mainly xylose, containing slight amounts of uronic acid, rhamnose, etc., and the xylooligosaccharide is the aforesaid oligosaccharide having a polymerization degree of from 2 to 10 or a composition containing it.

The oligosaccharide as described above is, for example, prepared as follows. That is, after adjusting the pH of a 2.5% (w/v) aqueous solution of commercially available xylan to 5.0, Meilase (trade name, made by Meiji Seika Kaisha, Ltd.) as an enzyme containing xylase was added to the solution in an amount of 10 mg per gram of xylase and the mixture was reacted for 48 hours at 40° C. In the reaction mixture were formed 66% oligosaccharide having a polymerization degree of from 2 to 7 and 34% oligosaccharide having polymerization degree of at least 8. Fractionation of the oligosaccharides could be performed by filtration. For example, the oligosaccharides having a polymerization degree of from 2 to 7 could be isolated from the reaction mixture by column chromatography using a column packed with Biogel P-2 (trade name, made by Bio-Rad Laboratories, California, U.S.A.).

Xylan is a polysaccharide containing xylose as the saccharide component and includes $\beta$-1,4-xylan wherein the bond between xyloses is mainly a $\beta$-1,4 bond and $\beta$-1, 3-xylan wherein the bond between xyloses is mainly a $\beta$-1, 3 bond. Also, $\beta$-1,4-xylan exists in corn cobs, rice straws, hemicellose A component of terrestrial plants etc., and $\beta$-1,3-xylan exists in red algae such as Rhodymenia palmata, etc., or green algae such as Caulerpa racemosa, etc. The xylooligosaccharide obtained by decomposing such a xylan with an acid or an enzyme is called $\beta$-1,3-xylooligosaccharide or $\beta$-14-xyloligosaccharide.

(3) Oligosaccharide obtained by decomposing polysaccharides of plants cell walls:

Cell wall polysaccharide of a plant is the cell wall itself of the plant or polysaccharides existing among the cells and is a mixture of polysaccharides such as cellulose, xyloglucan, xylan, $\beta$-glucan, arabinan, arabinogalactan, rhamnogalacturonan, pectin, arabinoxylan, polygalacturonic acid, galactan, etc. The oligosaccharide represents the decomposition products obtained by decomposing such a cell wall polysaccharide with an acid or an enzyme or an oligosaccharide as the main component of the decomposition products. The saccharides constituting the polysaccharide are glucose, xylose, arbinose, rhamnose, galactose, galactouronic acid, derivatives of galactouronic acid, mannose, etc., and are a mixture of oligosaccharides having a polymerization degrees of from 2 to 10.

Such an oligosaccharide is prepared as follows.

As the raw material for the cell wall polysaccharide, there are a plant itself, callus obtained from a plant, a culture fluid obtained by culturing callus, etc. Furthermore, an extract obtained by applying a pretreatment such as grinding to a plant and extracting polysaccharides from the ground plant using water, an aqueous alkali solution, a neutral aqueous salt solution, etc., as well as polysaccharides separated from the aforesaid extract using an organic solvent such as an alcohol, etc., followed by purification can also be used as the raw material.

The polysaccharide thus obtained is dissolved in water to form an aqueous solution thereof having a concentration of from 1 to 5%, and after adding thereto an acid such as hydrochloric acid of from 1 to 5% in concentration, the polysaccharide is hydrolyzed for 1 to 4 hours at 80° to 100° C., where by the-oligosaccharide can be formed in the decomposed liquid. In the case of using a plant or callus a raw material, an oligosaccharide-containing liquid can be prepared by grinding a plant or callus, adding from 1 to 5% acid such as hydrochloric acid, etc., to the ground product to perform hydrolysis for 1 to 6 hours at 80° to 100° C., and, after neutralizing the hydrolyzed product, removing the decomposed residues from the product by filtration, etc. Also, in the case of decomposing with an enzyme, the oligosaccharide can be obtained by adjusting the pH of an aqueous solution of from 1% to 5% cell wall polysaccharide obtained as described above or the ground product of a plant or callus, to the optimum pH for the action of an enzyme being used and decomposing it with an enzyme for 4 to 48 hours under the optimum temperature condition for the action of the enzyme. As an enzyme which is used for the aforesaid purpose, an enzyme having decomposing activities to various kinds of substrates is preferably used since the cell wall polysaccharide contains various kinds of polysaccharides, and as the enzyme meeting these purposes, a cellulase preparation is particularly preferred. Examples of such an enzyme are Meicelase (trade name, made by Meiji Seika Kaisha, Ltd.), Cellulase Onozuka R-10 (trade name, made by Kinki Yakult Seizo K.K.), Cellusase Ap (trade name, made by Amano Seiyaku K.K.) Macerozyme (trade name, made by Yakult Co., Ltd.), etc. It is preferred that the added amount of the enxyme is from 1 mg to 50 mg per gram of a polysaccharide as a substrate.

(4) Polygalacturonic Acid Oligosaccharide:

This oligosaccharide is a decomposition product obtained by decomposing polygalacturonic acid with an acid or an enzyme or an oligosaccharide which is the main component of the decomposition product. The saccharide component thereof is galacturonic acid the polymerization degree of the oligosaccharide is from 2 to 10.

The oligosaccharide is prepared as follows.

Polygalacturonic acid is dissolved in water to form a 2% aqueous solution of polygalacturonic acid, hydrochloric acid is added to the solution at a concentration of 2%, and after performing the hydrolysis with the acid for 3 hours at temperature of from 90° to 100° C., the reaction mixture thus obtained is neutralized, the decomposition residues are filtered off from the reaction mixture, and the filtrate obtained is concentrated to provide an aqueous solution containing polygalacturonic acid oligosaccharide.

In the case of decomposing with an enzyme, the oligosaccharide can be prepared by adjusting the pH of a 2% aqueous solution of polygalacturonic acid to 5.0, adding thereto pectinase in an amount of 10 mg per gram of the substrate, and then decomposing the acid for 6 hours at 50° C.

The solution containing the oligosaccharide thus obtained can be, if necessary, decolored by active carbon or purified by gel filtration or an ion-exchange resin according to the purpose thereof.

(5) Pecton Oligosaccharide:

This oligosaccharide is a decomposition product obtained by decomposing pectin with an acid or an enzyme, or is an oligosaccharide which is the main component of the decomposition product. The saccharide components constituting the oligosaccharide are galacturonic acid and galacturonic acid methyl ester, and the polymerization degree thereof is from 2 to 10.

The pectin oligosaccharide can be prepared by the same manner as in the case of preparing polygalacturonic acid oligosaccharide described above.

(6) Glucomannan Oligosaccharide:

This oligosaccaride is a decomposition product obtained by hydrolyzing glucomannan or konjac (Amorphophallus konjac C. Koch) containing glucomannan with an enzyme capable of having glucomannan as a substrate, such as endo-1 4-β-D-mannase, etc., or by hydrolyzing the aforesaid material with an acid such as hydrochloric acid, etc., or an oligosaccharide which is the main componennt of the decomposition product. The saccharide components constituting the oligosaccharide are mannose and glucose. Glucomannan oligosaccharide includes the aforesaid oligosaccharide having a polymerization degree of from 2 to 10 and a composition containing the oligosaccharide.

The oligosaccharide can be prepared, for example, by the following manner.

As the raw material, glucomannan or kojac containing glucomannan can be used. For decomposing glucomannan, a method of decomposing it with an enzyme such as mannase, etc., can be applied. For example, glucomannan oligosaccharide can be prepared by adding 100 parts of water to 2 parts of glucomannan to form an aqueous solution of glucomannan, adding thereto 3 parts of concentrated hydrochloric acid, performing the hydrolysis for 1 to 4 hours at 90° to 100° C., filtering the reaction mixture, and, after neutralizing the filtrate thus formed with sodium hydroxide, concentrating the filtrate.

Also, in the case of decomposing with mannase, the oligosaccharide can be prepared by dissolving 2 parts of glucomannan in 100 parts of water, adjusting the pH of the solution to the optimum value for the action of the enzyme, and performing the reaction for 10 to 48 hours at the optimum temperature for the action of the enzyme. As the mannase, an enzyme produced by *Rhizopus niveus*, an enzyme produced by *Aspergillus niger*, a commercially available cellulase preparation having a mannase activity, etc., can be used.

The reaction mixture obtained as described above can be decolored using active carbon, etc., or desalted using an ion-exchange resin.

Glucomannan is also called "kojac manna" and the saccharide components constituting it are glucose and mannose. The olgosaccharide obtained by decomposing such polysaccharides is a hetero-oligosaccharide composed of glucose and mannose, typified by epicellobiose (O-β-D-glucopyranasyl-(1-4)-D-mannopyranase).

(7) Agarooligosaccharide:

This oligosaccharide is the decomposition product formed by decomposing agar, agarose, agaropectin, or algae belonging to red algae and containing the aforesaid component, such as Gelidium amansii Lamouroux, etc., with an acid such as hydrochloric acid, etc., or an enzyme such as agarase, etc., or an oligosaccharide which is the main component of the decomposition product. The saccharide components constituting the oligosaccharide are galactsose, 3, 6-anhydrogalactose, 6-O-methylgalactose, xylose, and glucuronic acid. Agarooligosaccharide includes the aforesaid oligosaccharide having a polymerization degree of from 2 to 20 and a composition containing the oligosaccharide.

The oligosaccharide is prepared by, for example, as follows.

The pH of 1% (w/v) aqueous solution of commercially available agarose is adjusted to 6.0, agarase is added to the solution in an amount of 40 units per gram of agarose, and, after performing the reaction for 72 hours at 40° C. the reaction mixture obtained is decolored. Thereafter, by desalting with ion-exchange resin, the agarooligosaccharide is obtained.

(8) Celloligosaccharide:

This oligosaccharide is the decomposition product obtained by hydrolyzing cellulose, a skeleton material of a plant containing cellulose, the cell membranes of microorganisms, the mantle membranes of an acidian (Viscum album L.), Booshuu acidian, etc., or a cellulose derivative such as carboxymethyl cellulose, etc., with an enzyme such as cellulose, etc., or an acid such as hydrochloric acid, sulfuric acid, etc., or an oligosaccharide which is the main component of the decomposition product.

The saccharide components constituting the oligosaccharide are glucose and its derivatives. Cello-oligosaccharide includes the aforesaid oligosaccharide having a polymerization degree of from 2 to 10 and a composition of the oligosaccharide.

Such a composition is prepared, for example, as follows. After adding 2 parts of hydrochloric acid and 2 parts of sulfuric acid to one part of powdered cellulose (Avicell, trade name, made by Asahi Kasei Kogyo Co., Ltd.) as raw material to dissolve the cellulose, 12 parts of hydrochloric acid is further added to the solution and the reaction is performed for 5 hours at 20° to 25° C. After the reaction is completed, the reaction mixture obtained is neutralized, desalted by an ordinary manner such as gel filtration and electrodialysis, concentrated, and, if necessary, dried to provide cellooligosaccharide.

(9) Inulooligosaccharide:

This oligosaccharide is a decomposition product obtained by hydrolyzing inulin or Helianthus tuberosus L. containing inulin with inulinase or an acid such as hydrochloric acid, oxalic acid, etc., or an oligosaccharide which is the main component of the decomposition product. The saccharide components constituting the oligosaccharide are fructose and glucose. Inulooligosaccharide includes the above-described oligosaccharide having a polymerization degree of from 2 to 10 and a composition thereof.

The oligosaccharide is prepared, for example, as follows.

That is, after adding 4 parts of water to one part of Helianthus tuberosus L. followed by grinding, oxalic acid is added thereto at a final concentration of 0.1N and the hydrolysis is performed for one hour at 60° C. Thereafter, the reaction mixture is neutralized with calcium carbonate and, after removing residues by filtration, the filtrate is concentrated and, if necessary, dried to provide inulooligosaccharide.

(10) Mannan Oligosaccharide:

This oligosaccharide is a decomposition product of mannan (β-1,4-mannan, β-1,3-mannan, α-1,6-mannan, etc.,), the seed of Phytelephas macrocarpa containing mannan, Codium mucronatum, metabolized product of yeast or mold, etc., with an acid or an enzyme such as mannase, etc., or an oligosaccharide which is the main component of the decomposition product. The saccharide component of the oligosaccharide is mannose. Mannan oligosaccharide includes the aforesaid oligosaccharide having a polymerization of from 2 to 10 and a composition containing the oligosaccharide.

The oligosaccharide is prepared, for example, as follows.

That is, after dissolving 4 parts of mannan of yeast in 100 parts of hot water, 100 parts of an aqueous solution of 1N hydrochloric acid is added to the solution and the hydrolysis is performed for 2 hours at 90° to 100° C.

After the reaction is completed, the reaction mixture is neutralized to provide the decomposition product. If necessary, the oligosaccharide having a polymerization degree of from 2 to 10 can be separeted from the reaction mixture by column chromatography using a column packed with Biogel P-2.

(11) Fucoidan Oligosaccharide:

This oligosaccharide is the decomposition product of fucoidan or fucan sulfuric acid with an acid or an enzyme or an oligosaccharide which is the main component of the decomposition product. The saccharide component constituting it is fucose. Fucoidin oligosaccharide includes the aforesaid oligosaccharide having a polymerization degree of from 2 to 10 and a composition containing the oligosaccharide.

The oligosaccharide is prepared, for example, as follows.

That is, after dissolving 4 parts of fucoidan originated from brown algae (Phaeophyceae) in 100 parts of hot water, 100 parts of an aqueous solution of 1N hydrochloric acid is added to the solution and the hydrolysis is performed for 2 to 4 hours at 90° to 100° C. After the reaction is over, the reaction mixture is neutralized to provide the decomposition product. Also, if necessary, the oligosaccharide a polymerization degree of from 2 to 10 can be separated from the reaction product by column chromatography using column packed with Biogel P-2.

(12) Gum Arabic Oligosaccharide:

This oligosaccharide is a decomposition product obtained by decomposing gum arabic with an acid or an enzyme or an oligosaccharide which is the main component of the decomposition product. The saccharide components constituting the oligosaccharide are galactose, arabinose, rhamnose, and glucuronic acid. Gum arabic oligosaccharide includes the aforesaid oligosaccharide having a polymerization degree of from 2 to 10 and a composition containing the oligosaccharide.

The oligosaccharide is prepared, for example, as follows.

That is, after dissolving 4 parts of gum arabic in 100 parts of hot water, 100 parts of an aqueous solution of 1N hydrochloric acid is added to the solution and the hydrolysis is performed for 2 hours at 90° to 100° C. After the reaction is completed, the reaction mixture is neutralized to provide the decomposition product. Also, if necessary, the oligosaccharide having a polymerization degree of from 2 to 10 can be separated from the reaction product by column chromatography using a column packed with Biogel P-2.

(13) Polyethylene Glycol Alginic Acid Oligosaccharide:

This oligosaccharide is a decomposition product obtained by decomposing polyethylene glycol alginic acid with an acid or an enzyme, or an oligosaccharide which is the main component of the decomposition product. The saccharide components constituting the oligosaccharide are polyethylene glycol guluronic acid and polyethylene glycol mannuronic acid. Polyethylene glycol alginic acid oligosaccharide includes the aforesaid oligosaccharide having a polymerization degree of from 2 to 10 and a composition containing the oligosaccharide.

The oligosaccharide is prepared, for example, as follows.

That is, after dissolving 4 parts of polyethylene glycol alginic acid in 100 parts of hot water, 100 parts of an aqueous 1N hydrochloric acid solution is added to the solution and the hydrolysis is performed for 2 to 4 hours at 90° to 100° C. After the reaction is completed, the reaction mixture is neutralized to provide the decomposition product. Also, if necessary, the oligosaccharide having a polymerization degree of from 2 to 10 can be separated from the decomposition product by column chromatography using a column packed with Biogel P-2.

(14) Carrageenan Oligosaccharide:

This oligosaccharide is a decomposition product obtained by decomposing carrageenan or red algae belonging to the genus *Chondrus crispus*, genus *Cigartina tenella*, genus Hypneacease, etc., with an acid or an enzyme, or an oligosaccharide which is the main component of the decomposition product. The saccharide component constituting the oligosaccharide is a polymer of carrabiose. Carrageenan oligosaccharide includes the aforesaid oligosaccharide having a polymerization degree of from 2 to 10 and a composition containing the oligosaccharide.

The oligosaccharide is prepared, for example, as follows.

That is, after dissolving 4 parts of carrageenan in 100 parts of hot water, 100 parts of an aqueous 1N hydrochloric acid solution is added to the solution and the hydrolysis is performed from 2 hours at 90° C. to 100° C. After the reaction is completed, the reaction mixture is neutralized to provide the decomposition product. Also, if necessary, the oligosaccharide having a polymerization degree of from 2 to 10 can be separated from the decomposition product by column chromatography using a column packed with Biogel P-2.

(15) Oligodsccharide obtained by decomposing polysaccharide produced by microorganisms:

This oligosaccharide is a decomposition product obtained by decomposing the polysaccharide produced by microorganisms belonging to the genus Azotobacter, genus Enterobacter, genus Agrobacterium, genus Rhizobium, genus Pseudomonas, genus Xanthomonas, genus Zoogloea, genus Aspergillus, genus Saccharomyces, etc., with an acid or an enzyme, or an oligosaccharide which is the main component of the decomposition product. The oligosaccharide has also an action of accelerating the growth of plants.

The oligosaccharide is generally produced as follows.

That is, the oligosaccharide is produced by cultivating microorganisms producing the desired extracellular polysaccharide in a culture medium containing a carbon source such as sucrose, maltose, glucose, lactose, glycerol, etc., and a nitrogen source such as yeast extract, peptone, ammonium sulfate, etc., together with, if necessary, vitamins, inorganic salts, etc., after removing cells or mycelia by a means such as centrifugal separation, filtration, etc., adding an organic solvent such as ethanol, methanol, acetone, etc., to the supernatant liquid in an amount of 2 to 4 parts by volume to one part of the supernatent to precipitate and separate polysaccharide formed or concentrating polysaccharide by means of ultrafiltration, and then decomposing the polysaccharide thus separated or concentrated with the addition of an acid. As the acid, hydrochloric acid, sulfuric acid, etc., is used at a concentration of from 0.1N to 1.0N. The reaction temperature for the decomposition of the polysaccharide is from 50° C. to 120° C. and the reaction time is from 10 minutes to 10 hours, These conditions are properly selected according to the kind of the polysaccharide.

The decomposition product thus obtained can be used as it is for the purpose of this invention but it is possible to separate and purify the oligosaccharide having a polymerization degree of from 2 to 20 formed in the decomposition product by means such as gel filtration or ion-exchange chromatography using a column packed with Sephadex, Biogel, etc., for the purpose of this invention.

In more detail, each material can be produced, for example, by the following method.

(a) Plant growth-accelerating oligosaccharide obtained by decomposing polysaccharide produced by microorganisms belonging to the genus Azotobacter:

After subjecting *Azotobacter vinelandii* IAM 1078 to shaking culture in a liquid culture medium containing 0.025% $KH_2PO_4$, 0.0005% $Na_2MoO_4 \cdot 2H_2O$, 0.0125% $MgSO_4 \cdot 7H_2O$, 0.0005% $MnSO_4 \cdot 4H_2O$, 0.025% NaCl, 0.0005% $FeSO_4 \cdot 7H_2O$, and 2.0% sucrose for 5 days at 30° C., the culture liquid obtained is subjected to centrifugal separation at 10,000 G for 30 minutes to remove the cells, and after concentrating the supernatant liquid, 3 parts by volume of ethanol is added to 1 part of the concentrated liquid to precipitate polysaccharide formed, and the precipitates are separated and dried to provide a polysaccharide. The polysaccharide thus obtained is dissolved in water to form a 0.1% aqueous solution of the polysaccharide and after adding hydrochloric acid to the aqueous solution at a final concentration of 0.1N, the hydrolysis of the polysaccharide is performed for 6 hours at 100° C. Thereafter, by neutralizing the reaction mixture with sodium hydroxide, the desired decomposition product can be obtained.

The decomposition product thus obtained can be used as it is for the purpose of this invention but, if necessary, the decomposition product is desalted by gel filtration, etc., and further the-oligosaccharide having a polymerization degree of from 2 to 20 which is the main component in the decomposition product can be separated and purified for use in this invention. The chemical structure of the oligosaccharide obtained by decomposing a polysaccharide produced by Azotobacter vinelandii is reported by G. H. Cohen, etc., in *Journal of Bacteriolology*, 88, 329(1964), etc. The saccharide components constituting the oligosaccharide are galacturonic acid, glucose, rhamnose, etc.

(b) Plant growth-accelerating oligosaccharide obtained by decomposting a polysaccharide produced by microorganisms belonging to the genus Agrobacterium:

After subjecting *Aagrobacterium tumefaciens* IAM 1037 to shaking culture in a liquid culture medium containing 1.0% mannitol, 0.1% $MgCl_2$, 0.1% glutamic acid, 0.1% $K_2HPO_4$, 0.02% $MgSO_4 \cdot 7H_2O$, 0.004% $CaCl_2$, and, as minor nutrients, 10γ of biotin, 100γ of thiamine, 2.5 mg of $FeCl_3 \cdot 6H_2O$, 0.01 mg of $H_3BO_3$, 0.01 mg of $ZnSO_4 \cdot 7H_2O$, 0.01 mg of $cocl_2 \cdot 2H_2O$ per liter of the culture medium, for 5 days at 25° C., the culture liquid obtained is diluted with 1 liter of water per liter of the culture liquid, the diluted liquid is subjected to centrifugal separation at 10,000 G for 40 minutes to remove the cell, and after concentrating by 3-fold the supernatent liquid formed, ethanol is added to the concentrated liquid in an amount of thrice the volume of the liquid to precipitate a polysaccharide formed. Then, by separating and drying the product, a polysaccharide can be obtained in an amount of 1 to 2 g per liter of the culture liquid.

The polysaccharide thus obtained is dissolved in water to form an aqueous solution thereof at a concentration of 1%, hydrochloric acid is added to the solution at a final concentration of 0.1N and the hydrolysis of the polysaccharide is performed for 6 hours at 100° C. Then, by neutralizing the reaction mixture obtained with sodium hydroxide, the desired decomposition product can be produced.

The decomposition product thus obtained can be used as it is for the purpose of this invention but, if necessary, the oligosaccharide having a polymerization degree of from 2 to 20 can be separated and purified from the decomposition product by desalting and purification means such as gel filtration, etc., for use in this invention. The chemical structure of the polysaccharide produced by microorganisms belonging to the genus Agrobacterium or the partial decomposition product thereof is reported by L. P. T. M. Zevenhuizen in *Carbohydrate, Research*, 24, 409(1973). The saccharide components constituting the oligosaccharide are glucose, galactose, pyruvic acid, uronic acid, etc.

(c) Plant growth-accelerating oligosaccharide obtained by decomposing a polysaccharide produced by microorganisms belonging to the genus Rhizobium:

After subjecting *Rhizobium meliloti* IAM 12611 to shaking culture in a liquid culture medium containing 1.0% mannitol, 0.1% $MgCl_2$, 0.1% glutamic acid, 0.1% $K_2HPO_4$, 0.02% $MgSO_4 \cdot 7H_2O$, 0.004% $CaCl_2$, and, as minor nutrients, 10γ of biotin, 100γ of thiamine, 2.5 mg of $FeCl_3 \cdot 6H_2O$, 0.01 mg of $H_3BO_3$, 0.01 mg of $ZnSO_4 \cdot 7H_2O$, 0.01 mg of $Cocl_2 \cdot 7H_2O$, 0.01 mg of $CuSO_4 \cdot 5H_2O$, and 0.01 mg of $Na_2MoO_4 \cdot 2H_2O$ per liter of the culture medium for 5 days at 25° C., the culture liquid thus obtained is diluted with 1 liter of water per liter of the culture liquid, the diluted liquid is subjected to centrifugal separation at 10,000 G for 40 minutes to remove mycelia, and after concentrating by 3-fold the supernatant liquid formed, ethanol is added to the concentrate in an amount of thrice the volume of the liquid to precipitate a polysaccharide formed. By separating and drying the precipitates, a polysaccharide can be obtained in an amount of 0.4 to 0.8 g per liter of the culture liquid.

The polysaccharide thus obtained is dissolved in water to form an aqueous solution thereof having a concentration of 0.1%, hydrochloric acid is added to the solution at a final concentration of 0.1N, and the hydrolysis of the polysaccharide is performed for 6 hours at 100° C. By neutralizing the reaction mixture obtained with sodium hydroxide, the desired decomposition product can be obtained.

The decomposition product thus obtained can be used as it is for the purpose of this invention but, if necessary, the oligosaccharide having a polymerization degree of from 2 to 20 is separated from the decomposition product and purified using a desalting and purification means such as gel filtration, etc., for use in this invention.

The chemical structure of the polysaccharide produced by microorgansms belonging to genus Rhizobium or the the partial decomposition product thereof is reported by L. P. T. M. Zevenhuiten in *Journal of General Microbiology*, 68, 239(1971), etc.

The sacchride components of the oligosaccharide are glucose, galactose, pyrvic acid, glucuronic acid, etc.

(d) Plant growth-accelerating oligosaccharide obtained by decomposing a polysaccharide produced by microorganisms belonging to the genus Enterobacter:

After subjecting *Enterobacter cloacae* FERM BP1529 to shaking culture in a liquid culture medium containing lactose, 0.5% peptone, 0.1% $KH_2PO_4$, 0.05% $MgSO_4 \cdot 7H_2O$, and 0.0033% Rose Bengale for 3 days at 30° C., the culture liquid obtained is subjected to centrifugal separation to remove the cells and after concentrating by 3-fold the supernatant liquid, ethanol is added to the concentrated liquid in an amount of thrice the volume of the liquid to precipitate a polysaccharide formed. By separating the precipitates followed by drying, the polysaccharide is obtained in an amount of 0.6 to 1.2 g per liter of the culture liquid.

The polysaccharide thus obtained is dissolved in water to form an aqueous solution thereof at a concentration of 0.5%, and after adding thereof hydrochloric acid at a final concentration of 0.1N, the hydrolysis of the polysaccharide is performed for 4 hours at 100° C., and the reaction mixture is neutralized with sodium hydroxide to provide the desired decomposition product.

The decomposition product thus obtained can be used as it is for the purpose of this invention but, if necessary, the oligosaccharide having a polymerization degree of from 2 to 20 can be separated from the decomposition product and purified by desalting and purification means such as gel filtration for use in this invention.

The saccharide components constituting the polysaccharide produced from *Enterobacter cloacae* are glucose, galactose, rhamnose, fucose, mannuronic acid, etc.

The polysaccharide produced from *Enterobacter cloacae* has a plant growth-accelerating action by itself as shown in Example 3 described hereinbelow but the oligosaccharide obtained by decomposing the polysaccharide shows more increased plant growth-accelerating action.

(e) Plant growth-accelerating oligosaccharide obtained by decomposing a polysaccharide produced by microorganisms belonging to the genus Zooloea:

A polysaccharide produced from *Zoogloea ramigera* (commerically availabe product, made by Sigma Co.) is dissolved in water to form 0.1% aqueous solution of the polysaccharide, and after adding thereto hydrochloric acid at a final concentration of 0.1N, the hydrolysis thereof is performed for 4 hours at 100° C., and the reaction mixture obtained is neutralized by sodium hydroxide to provide the desired decomposition product.

The decomposition product-thus obtained can be used as it is for the purpose of this invention but, if necessary, the oligosaccharide having a polymerization degree of from 2 to 20 can be separated from the decomposition product and purified by desalting and purification means such as gel filtration, etc., for use in this invention.

The chemical structure of the polysaccharide produced from *Zoogloea ramigera* is reported by F. Ikeda, et al. in *European Journal of Biochemistry*, 123, 437(1982) and the saccharide components thereof are glucose, galactose, pyruvic acid, etc.

(f) Plant growth-accelerating oligosaccharide obtained by decomposing a polysaccharide produced from microorganisms belonging to the genus Xanthomonas:

The polysaccharide produced by the microorganisms belonging to the genus Xanthomonas is commercially available as Xanthan Gum (made by Sigma Co.).

Xanthan Gum is dissolved in water to form a 1.0% aqueous solution of the polysaccharide, and after adding thereto hydrochloric acid at a final concentration of 0.1N, the hydrolysis is performed for 7 hours at 100° C., and the reaction mixture obtained is neutralized with sodium hydroxide to provide the desired decomposition product.

The decomposition product-thus obtained can be used as it is for the purpose of this invention but, if necessary, the oligosaccharide having a polymerization degree of from 2 to 20 can be separated from the decomposition product and purified using desalting and purification means such as gel filtration etc., for use in this invention.

There are many reports on the chemical structure of Xanthan gum and the saccharide components thereof are glucose, mannose, glucuronic acid, pyruvic acid, acetic acid, etc.

(g) Plant growth-accelerating oligosaccharide obtained by decomposing a polysaccharide produced by microorganisms belonging to the genus Pseudomonas:

The polysaccharide produced by *Pseudomonas elodea* is commercially available as Gellan Gum (made by Sanei Kagaku Kogyo K.K.).

Gellan Gum is dissolved in water to form a 0.1% aqueous solution of the polysaccharide, and after adding thereto hydrochloric acid at a final concentration of 1.0N, the hydrolysis is performed for 15 minutes at 120° C., and the reaction mixture is neutralized with sodium hydroxide to provide the desired decomposition product.

The decomposition product thus obtained can be used as it is for the purpose of this invention but, if necessary, the oligosaccharide having a polymerization degree of from 2 to 20 can be separated from the decomposition product and purified by a desalting and purification means such as gel filtration for use in this invention.

Gellan Gum itself shows a gelatinous state as a 0.1% aqueous solution thereof and is used as a substitute for agar-agar. It is reported that when a callus of a plant or a young plant is grown by Gellan Gum in such a state, the growth of the plants may be accelerated to some extent but the inventors have found that the decomposition product containing the oligosaccharide as the main component obtained by decomposing the polysaccharide has a plant growth-accelerating activity of 100 times higher than that with the under composed polysaccharide, Gellan Gum (as shown in Example 42 below).

(h) Plant growth-accelerating oligosaccharide obtained by decomposing a polysaccharide produced by microorganisms belonging to the genus Aspergillus:

The polysaccharide produced by *Aspergillus niger* is commercially available as Nigeran (made by Sigma Co.).

Nigeran is dissolved in water to form an aqueous solution of 0.1% in concentration, and after adding thereto hydrochloric acid at final concentration of 0.1N, the hydrolysis is performed for 4 hours at 100° C., and the reaction mixture is neutralized with sodium hydroxide to provide the desired decomposition product.

The decomposition product thus obtained can be used as it is for the purpose of this invention but, if necessary, the oligosaccharide having a polymerization of from 2 to 20 can be separated from the decomposition product and purified by desalting and purification means such as gel filtration, etc., for use in this invention.

The chemical structure of Nigeran is reported by S. A. Barker, et al, in *Journal of Chemical Society*, 2448(1957). The saccharide components thereof are polysaccharides formed by α-1,4 bonding or α-1,3 bonding of glucose.

(i) Plant growth-accelerating oligosaccharide obtained by decomposing a polysaccharide produced by microorganisms belonging to the genus Saccharomyces:

The polysaccharide produced by *Saccharomyces cerevisiae* is commercially available as Mannan (made by Sigma Co.).

Mannan is dissolved in water to form an aqueous 1% solution thereof and, after adding thereto hydrochloric acid at final concentration of 0.1N, the hydrolysis is performed for 6 hours at 100° C. and the reaction mixture formed is neutralized with sodium hydroxide to provide the desired decomposition product.

The decomposition product thus obtained can be used as it is for the purpose of this invention but, if necessary, the oligosaccharide having a polymerization degree of from 2 to 20 can be separated from the decomposition product and purified by desalting and purification means such as gel filtration, etc., for use in this invention.

The various oligosaccharides having an action of accelerating the growth of plants described above are applied to plants as follows. That is, the oligosaccharide is applied to plants by coating it on the seeds, etc., at a ratio of from 5γ to 100γ per grain of the seed, applying to the surfaces of leaves of a plant an aqueous solution of 20 γ/ml to 200 γ/ml thereof, applied into the soil as an aqueous solution of 30 γ/ml 350 γ/ml at a ratio of from 0.5 kg to 5.0 kg per hectare, mixing it with a liquid fertilizer for hydroponics at a concentration of 2.5 γ/ml to 250 γ/ml, or coating it on or mixing it with a solid fertilizer such as a solid chemical fertilizer at a ratio of from 0.1% to 0.5%. Thus, the growth of the roots, stalks, and leaves of plants is accelerated to thereby improve the yield of the plants. Also, the harvests thus obtained have such features that they are excellent in taste and liking, and the freshness thereof can be maintained for a relatively long period of time. Furthermore, as plants suitable for this invention, there are green plants such as Kaiware Daikon, stone parsley, Chinese cabbage, lettuce, spinach, radish, potato, taro, etc., cerals such as rice plant, wheat, corn plant, etc., and other agricultural products such as petals, fruits, etc.

Now, the invention will be described in detail by the following examples.

EXAMPLE 1

An oligosaccharide (unheated product) was prepared by adding alginic acid lyase (Abalone Acetone Powder) to alginic acid at a ratio of 4,000 u/g of alginic acid and reacting them for 48 hours at pH 7.0 and 40° C. Thereafter, the oligosaccharide was heat-treated for 2 hours at 120° C. After heat-treatment, the reaction mixture was neutralizaed to pH 7.0. Then, the plant growth-accelerating action of the alginic acid oligosaccharide before and after heating was determined using Kaiware Daikon.

36 seed grains of Kaiware Daikon were placed on a synthetic resin mat contained in a glass vessel and after adding 70 ml of tap water, they were cultivated for 6 days at 23° C. (cultivated in the dark for first 4 days and then under the irradation of light of 5,000 lux for 2 days). Each alginic acid oligosaccharide was added at the indicated ratios of from 2.5% to 0.000025% to the amount of the tap water. The results obtained are shown in Table 1 below.

In addition, the numerical values in Table 1 are the mean values of the stalk-leave length(cm) and the root length(cm) of the plant cultivated in each case with those of the stalk-leaf length and the root length of the plant cultivated without the aliginic acid oligosaccharide, etc. being 100 (n=36)

TABLE 1

| Added Amount (%) of Alginic Acid Oligoscaccharide | Product Heated at 120° C. and pH 2.0 | | Unheated Product | |
|---|---|---|---|---|
| | Stalk-Leaf Length (%) | Root Length (%) | Stalk-Leaf Length (%) | Root Length (%) |
| 2.5 | 80 | 91 | 90 | 84 |
| 0.25 | 135 | 325 | 140 | 297 |
| 0.025 | 138 | 520 | 134 | 517 |
| 0.0025 | 115 | 274 | 108 | 148 |
| 0.00025 | 108 | 143 | 101 | 120 |
| 0.000025 | 101 | 98 | 98 | 102 |
| Sodium Alginate 0.25 | — | — | 100 | 99 |

(—): Not investigated:

As shown in the above table, the alginic acid oligosaccharide accelerates the growth of both the stalk-leave and the root of the plant in each concentration condition as compared to the control group without adding the alginic acid oligosaccharide, and when the alginic acid oligosaccharide is heated for 2 hours at 120° C. and pH 3.0, the effect is increased in each case.

EXAMPLE 2

Two seed grans of honewort (Crytotaenia japonica) were placed on a synthetic resin mat of 4 cm×4 cm, and after immersing the mat in a liquid fertilizer containing 0.15% Otsuka House Fertilizer #1 and 0.1% Otsuka House Fertilizer #2, the seeds were cultivated for 10 days at 23° C. under the condition of 5,000 lux to perform the germination of the seeds and nursing, and the seedlings were transferred into a hydroponic culture apparatus, and cultivated for 2.5 months under conditions of 8,000 lux and 23 to 24° C.
The experiment groups used were as follows:
Control Group:
After nursing with the liquid fertilizer containing no aliginic acid oligosaccharide, the seedlings were cultivated with the liquid fertilizer containing no alginic acid oligosaccharide.
Aliginic Acid Oligosaccharide-Added Group:
After nursing with the liquid fertilizer with 0.025% alginic acid oligosaccharide added, the seedlings cultivated with the liquid fertilizer containing 0.025% alginic acid oligosaccharide.
In addition, the alginic acid oligosaccharide used in this Example was prepared by adding alginic acid lyase to an aqueous solution of sodium alginate (pH 7.0) at a ratio of 4,000 u/g of alginic acid, performing the reaction for 48 hours at 40° C., adjusting the pH of the reaction mixture to 3.0, heat-treating the reaction mixture for 2 hours at 120° C. and after cooling, neutralizing the product to pH 7.0.
The test results obtained are shown in Table 2.

TABLE 2

| Experiment Group | Mean Stem Length (cm) | Mean Root Length (cm) |
|---|---|---|
| Alginic Acid Oligosaccharide- Added Group | 27.3 | 2.8 |
| Control Group | 20.8 | 1.8 |
| | | (n = 20) |

As shown in the above table, the yield of honewort is increased by the addition of the alginic acid oligosaccharide.

EXAMPLE 3

Seeds of Kaiware Daikon coated with alginic acid oligosaccharide were prepared by spraying 1 part by weight of an aqueous solution containing 0.25% alginic acid oligosaccharide and 0.75% sodium alginate onto 1 part by weight of the seeds and drying in an air stream of from 40° to 50° C.
Then, 50 grains of the alginic acid oligosaccharide-coated seeds thus obtained were placed on a synthetic resin mat in a glass vessel and after adding thereto 70 ml of tap water, the seeds were cultivated for days in the dark at 23° C. and then for 2 days under irradiation of light of 5,000 lux.
For Control Group, uncoated seeds of cotyledons were placed on a synthetic resin mat and cultivated under the same cultivation conditions as above.
The results are shown in Table 3.

TABLE 3

| Experiment Group | Stalk-Leaf Length (cm) | Root Length (cm) |
|---|---|---|
| Coated Seed | 7.80 | 8.56 |
| | (118) | (164) |
| Control Group | 6.63 | 5.22 |
| | (100) | (100) |

Table 3 indicates that when the seeds coated with aliginic acid oligosaccharide in an amount of 2.5 mg per gram of the seeds were used, the growth of 118% in stalk-leaf length and 164% in root length was observed.

EXAMPLE 4

After placing 40 grains of the seeds of Chinese cabbage (Brassica Rapa var. pervidis) (breeding: Misugi cabbage) on 9 kg of black soil in a pot of 17 cm×60 cm×15 cm, the seeds were cultivated under natural conditions from June 15 to July 4. The experiment groups used were as follows.
Control Group:
Alginic acid oligosaccharide is not added.
Added Group:
After adding 3.6 liters of an aqueous solution of g of alginic oligosaccharide to 9 kg of black soil (0.25% alginic acid oligosaccharide to the amount of black soil), the seeds were cultivated in this soil.
The alginic acid oligosaccharide used in this example had been prepared by the same manner as in Example 2. The results obtained are shown in Table 4.

TABLE 4

| Experiment Group | Mean weight per stump of cabbage |
|---|---|
| Control Group | 4.9 ± 1.4 (100) |
| Added Group | 5.9 ± 1.6 (120) |

The numerical value in the parentheses is the value with the mean value of Control Group being defined as 100.
As shown in the above table, the yield increase of 20% by the addition of the alginic acid oligosaccharide to the soil was confirmed.

EXAMPLE 5

The seeds of corn (Indian corn) were sown in the soil at 36 grains per 33 m2 and cultivated for 3.5 months under natural conditions. The experiment groups used were as follows.
Control Group:
Alginic acid oligosaccharide is not added.
Added Group:
When the stalk-leaf length became 8 to 12 cm after germination, 6 g of alginic acid oligosaccharide was applied to the circumference of each root as an aqueous 0.05% solution thereof. Furthermore, after 1.5 months since then, 6 g of alginic acid oligosaccharide was additionally supplied by the same manner as above.
The alginic acid oligosaccharide used had been prepared by the same manner as in Example 2. The results obtained are shown in Table 5.

TABLE 5

| Experiment Group | Yield (kg) |
|---|---|
| Alginic Acid Oligosaccharide-Added Group | 23.8 |
| Control Group | 18.9 |

As shown in Table 5, the yield increase of 26% for corn by the application of the alginic acid oligosaccharide was observed.

EXAMPLE 6

After cultivating 100 grains of the seeds of cucumber (breeding: Kifujin) in a seedling-nursing tray for one week at 20° to 23° C., the seedlings were transferred into a pot (diameter 90 mm; height 76 mm) and further cultivated for two weeks. The seedlings thus obtained were transplanted in the soil with an interval of 80 cm and cultivated for 3 months under natural conditions. The experiment groups used were as follows.

Control Group:
Alginic acid oligosaccharide is not added.

Added Group:
After 3 days since the transferring of the seedlings into pot, alginic acid oligosaccharide was applied thereto as an aqueous solution thereof of 25 mg per pot in 50 ml of water. Also, after 3 weeks since the transplanting of the seedlings into soil, an aqueous solution of 50 ml of alginic acid oligosaccharide dissolved in 500 ml of water was additionally applied.

The alginic acid oligosaccharide used had been prepared by the same manner as in Example 2.

The results obtained are shown in Table 6.

TABLE 6

| Experiment Group | Yield (kg/stump) |
| --- | --- |
| Alginic Acid Oligosaccharide Added-Group | 5.7 (119) |
| Control Group | 4.8 (100) |

As shown in the above table, the yield of cucumber was increased to 119% by the application of the alginic acid oligosaccharide.

EXAMPLE 7

After transplanting 56 stumps of potato (breeding: Danshaku) into a test field of 10.8 m² per group and cultivating for 2 months, an aqueous solution of alginic acid oligosaccharide was applied twice onto the leaf surfaces thereof at the budding phase during the cultivation. A fertilizer and water were applied by an ordinary manner. The test groups were as follows.

| Test Group | Chemical Applied | Concentration of the chemical |
| --- | --- | --- |
| 1 | Alginic Acid oligosaccharide | 200 γ/ml |
| 2 | " | 20 γ/ml |
| 3 | " | 2.0 γ/ml |
| 4 | None (water only) | 0 |

The alginic acid oligosaccharide used for the test had been prepared by the same manner as in Example 2. Also, the transplantion of the stumps of potato was practiced on February 27, the application of the aqueous solution of the alginic acid oligosaccharide to the leaf surfaces thereof on April 28 and May 8, and cultivation was finished on May 29. the test results obtained are shown in Table 7.

TABLE 7

| Test Group | Yield for Potato (g/stump) | Content of Starch (%) |
| --- | --- | --- |
| 1 | 530.6 (114) | 10.03 (121) |
| 2 | 514.2 (111) | 9.87 (116) |
| 3 | 473.6 (102) | 9.50 (111) |
| 4 | 464.3 (100) | 8.54 (100) |

As shown in Table 7 above, the increase in the yield and the starch content was confirmed by the application of the alginic acid oligosaccharide onto the leaf surfaces at concentrations of from 200 γ/ml to 2.0 γ/ml.

EXAMPLE 8

After transplanting 200 stumps of onion into a test field of 9 m² per group and cultivating for 4 months, alginic acid oligosaccharide was applied thrice to the field once a month as an aqueous solution thereof at a ratio of 5.0 kg, 1 kg, or 0.5 kg per ha during cultivation. A fertilizer and water were applied by an ordinary manner. The test groups used were as follows.

| Test Group | Chemical Applied | Concentration And Applied Amount |
| --- | --- | --- |
| 1 | Alginic Acid oligosaccharide | 335 γ/ml 5.0 kg/ha |
| 2 | " | 67 γ/ml 1.0 kg/ha |
| 3 | " | 3 γ/ml 0.5 kg/ha |
| 4 | None (water only) | |

The alignic acid oligosaccharide used had been prepared by the same manner as in Example 2.

The test results obtained are shown in Table 8.

TABLE 8

| Test Group | Yield for Onion (g/stump) |
| --- | --- |
| 1 | 271.6 (118%) |
| 2 | 263.4 (114%) |
| 3 | 242.6 (105%) |
| 4 | 230.6 (100%) |

As shown in Table 8 above, the yield increase of from 105% to 118% was observed by the application of an aqueous solution of the alginic acid oligosaccharide into the soil at various ratios of from 0.5 kg/ha to 1.5 kg/ha.

EXAMPLE 9

After seeding 250 grains of the seeds of green soybeans into a test field of 10.8 m2 per group, the seeds were cultivated according to an ordinary manner. In this case, before seeding, an aqueous solution of alginic acid oligosaccharide dissolved in an aqueous 0.75% sodium alginate solution was sprayed onto the seeds in an air stream of from 40° to 50° C. to coat the seeds with the alginic acid oligosaccharide at a ratio of 5γ, 50γ, or 100γ per seed grain and the seeds thus coated were used for the test. The test groups were as follows.

| Test Group | Coated amount (γ) of alginic acid oligosaccharide per seed grain |
| --- | --- |
| 1 | 100 |
| 2 | 50 |
| 3 | 5 |
| 4* | 0 |

(*): Control

The test results obtained are shown in Table 9.

TABLE 9

| Test Group | Yield for Soybean (g/stump) |
| --- | --- |
| 1 | 210 (111%) |
| 2 | 218 (1145) |
| 3 | 196 (108%) |
| 4 | 189 (100%) |

As shown in Table 9 the increase of the yield of from 4% to 15% was observed by coating the seeds with the alginic acid oligosaccharide at 5γ to 100γ per seed grain.

The alginic acid oligosaccharide used in the test had been prepared by the same manner as in Example 2.

EXAMPLE 10

After seeding 2 grains of the seeds of lettuce on a synthetic resin mat of 4 cm×4 cm and transferring the mat in to a hydroponic culture apparatus, the hydroponic cultivation was performed for 40 days under the irradiation of light of 5,000 lux.

For determining the action of alginic acid oligosaccharide, the liquid ferlizers containing alginic acid oligosaccharide at 25 γ/ml to 250 γ/l was used. The test groups were as follows.

| Test Group | Concentration (γ/ml) of alginic acid oligosaccharide |
|---|---|
| 1 | 250 |
| 2 | 100 |
| 3 | 50 |
| 4 | 25 |
| 5* | 0 |

(*): Control

The alginic acid oligosaccharide used in the test had been prepared by the same manner as in Example 2. The rest results obtained are shown in Table 10.

TABLE 10

| Test Group | Weight (g/stump) of stalk-leaf |
|---|---|
| 1 | 138.0 (140%) |
| 2 | 123.3 (110%) |
| 3 | 110.6 (112%) |
| 4 | 98.6 (100%) |
| 5 | 98.6 |

As is clear from Table 10, the yield increase of from 110% to 140% for lettuce was observed by practicing the hydroponic cultivation with the addition of the alginic acid oligosaccharide to the liquid fertilizer at the indicated ratio of from 25 γ/ml to 250 γ/ml.

EXAMPLE 11

In a pot of 17 cm×60 cm×15 cm was placed 8 kg of black soil, and after adding thereto 4 g of a chemical fertilizer or a mixture of the chemical fertilizer added with alginic acid oligosaccharide, 40 seed grains of spinach were sown in the soil and cultivated for 60 days under artificial conditions of 35,000 lux and 25° C.

The alginic acid oligosaccharide-added fertilizer had been prepared by spraying an aqueous solution of alginic acid oligosaccharide onto a chemical fertilizer followed by drying the test groups were as follows.

| Test Group | Added amount of alginic acid oligosaccharide in chemical fertilizer (%) |
|---|---|
| 1 | 0.5 |
| 2 | 0.25 |
| 3* | 9.1 |
| 4* | 0 |

(*): Control

The alginic acid saccharide used in the test had been prepared by the same manner as in Example 2.

The results obtained are shown in Table 11.

TABLE 11

| Test Group | Mean weight (g) of spinach per stump |
|---|---|
| 1 | 9.74 (145%) |
| 2 | 8.73 (130%) |
| 3 | 7.52 (112%) |
| 4 | 6.72 (100%) |

As is clear from Table 11, the yield increase of from 112% to 145% was observed by the application of the chemical fertilizers containing from 0.1% to 0.5% alginic acid oligosaccharide.

EXAMPLE 12

After dissolving 25 g of xylan in 1 liter of water and adjusting the pH of the solution to 5.0, a cellulase preparation containing xylase activity (Meicelase, trade name, made by Meiji Seika Kaisha, Ltd.) was added thereto at 10 mg per gram of xylanase and the reaction was performed for 48 hours at 40° C. After the reaction was over, the reaction mixture was heat-treated for 15 minutes at 100° C. to inactivate the enzyme and passed through a column packed with Biogel P-2 to remove the xylose portion and, at the same time, obtain 15 g of a powder of oligosaccharide having a polymerization degree of from 2 to 10. The composition of the saccharide was as shown in Table 12, wherein Xyl represents xylose, $Xyl_2$ xylobiose $Xyl_3$ xylotriose, and so on.

TABLE 12

| Saccharides | $Xyl_2$ | $Xyl_3$ | $Xyl_4$ | $Xyl_5$ | $Xyl_6$ | $Xyl_7$ | $Xyl_{7-10}$ |
|---|---|---|---|---|---|---|---|
| Content (%) | 7.4 | 9.7 | 15.1 | 8.1 | 14.1 | 12.1 | 33.5 |

The plant growth-accelerating action of the xylooligosaccharide thus obtained was determined for Kaiware Daikon.

That is, 36 grains of the seeds of Kaiware Daikon were placed on a synthetic resin mat set in a glass vessel and after adding thereto 70 ml of tap water, the seeds were cultivated for 4 days in the dark at 23° C. and then for 2 days under the irradiation of light of 5,000 lux. In this case, the xylooligosaccharide was added thereto at the indicated ratios of from 2.5% to 0.000025% to the amount of the tap water. The results obtained are shown in Table 13.

TABLE 13

| Added amount of Xylooligosaccharide (%) | Stalk-leaf Length (%) | Root Length (%) |
|---|---|---|
| 2.5 | 92 | 94 |
| 0.25 | 110 | 240 |
| 0.025 | 125 | 285 |

TABLE 13-continued

| Added amount of Xylooligosaccharide (%) | Stalk-leaf Length (%) | Root Length (%) |
|---|---|---|
| 0.0025 | 104 | 164 |
| 0.00025 | 102 | 109 |
| 0.000025 | 96 | 102 |
| | | (n = 36) |

The numeral values in Table 13 are the stalk-leaf length (cm) and the root length (cm) of cotyledons in each case with those of Kaiware Daikon cultivated under the condition of adding no xylooligasaccharide being defined as 100.

EXAMPLE 13

Two grains of the seeds of honewort (white stem honewort) were placed on a synthetic resin mat of 4 cm×4 cm and after immersing the mat in a liquid fertilizer containing 0.15% Otuka House fertilizer #1 and 0.1% Otsuka House fertilizer #2, the seeds were cultivated for 10 days under the irradiation of light of 5,000 lux at 23° C. to perform the germination and nursing. Thereafter, the seedlings were transplanted in a hydroponic cultivation apparatus and cultivated for 2.5 months under the conditions of 8,000 lux at 23° to 24° C. The experiment groups were as follows.

Control Group:
After nursing the seeds with the liquid fertilizer containing no xylooligosacchaaride, the seedlings were cultivated with the liquid fertilizer containing no xylooligosaccharide.

Xylooligosaccharide-Added Group:
After nursing the seeds with the liquid fertilizer containing 0.025% xylooligosaccharide, the seedlings were cultivated with the liquid fertilizer containing 0.025% xylooligosaccharide.

The xylooligosaccharide used in the test was prepared by the same manner as in Example 12.

The results obtained are shown in Table 14.

TABLE 14

| Experiment Group | Mean Stem Length (cm) | Mean Root Length (cm) |
|---|---|---|
| Xylooligosaccharide-Added Group | 24.2 | 2.3 |
| Control Group | 20.8 | 1.8 |
| | | (n = 20) |

As is clear from Table 14, the yield increase of honewort was observed by the addition of the xylooligosaccharide.

EXAMPLE 14

Seeds of Kaiware Daikon was coated with xylooligosaccharide at the indicated ratio of from 2.5 γ to 100 γ per grain of the seed by spraying 1 part by weight of the aqueous solutions containing from 0.7% to 0.025% xylooligosaccharide and 0.75% sodium alginate onto 1 part by weight of the seeds and drying the seeds in an air stream of 40° to 50° C.

After placing 50 grains of the xylooligosaccharide-coated seeds thus obtained on a synthetic resin mat set in a glass vessel and adding thereto 70 ml of tap water, the seeds were cultivated for 4 days in the dark of 23° C. and then for 2 days under the irradiation of light at 5,000 lux.

For Control Group, seeds of Kaiware Daikon without being coated with xylooligosaccharide were cultivated under the same conditions as above.

The results obtained are shown in Table 15.

TABLE 15

| Coated Amount of Xylooligosaccharide per Grain of Seed (γ) | Mean Stalk-Leaf Length (cm) | Mean Root Length (cm) |
|---|---|---|
| 100 | 7.74 (117) | 8.54 (164) |
| 50 | 7.76 (117) | 8.48 (163) |
| 25 | 7.15 (108) | 7.54 (145) |
| 5 | 6.94 (105) | 6.22 (119) |
| 2.5 | 6.70 (101) | 5.41 (104) |
| Control | 6.64 (100) | 5.21 (100) |

The numeral values in the parentheses are values of each case with the mean values of the Control Group being defined as 100.

As is clear from Table 15, the use of the seeds coated with xylooligosaccharide at from 5γ to 100γ per grain of the seed showed the growth acceleration action of from 105% to 117% in stalk-leaf length and from 119% to in root length as compared with the Control Group of using the seeds without being coated with xylooligosaccharide.

EXAMPLE 15

After sowing 40 grains of the seeds of Chinese cabbage (Brassica Rapa var. pervidis) (breeding: Misugi cabbage) into 9 kg of black soil in a pot of 17 cm×60 cm×15 cm, the seeds were cultivated for 30 days under natural conditions. The experiment groups were as follows.

Control Group:
Xylooligosaccharide is not added.

Added Group:
After adding an aqueous solution containing 22 g or 2.2 g of xylooligosaccharide in 3.6 liters of water to the black soil and then adding thereto 0.25% or 0.025% xylooligosaccharide, the seeds were cultivated in the soil.

The xylooligosaccharide used in the test had been prepared by the same manner as in Example 12.

The results are shown in Table 16.

TABLE 16

| Experiment Group | Mean weight per stump of Chinese cabbage |
|---|---|
| Control Group | 4.9 ± 1.4 (100) |
| 0.25% Added Group | 5.6 ± 1.2 (114) |
| 0.025% Added Group | 5.1 ± 1.6 (104) |

The numeral values in the parentheses are values of each case with the mean value of the Control Group being defined as 100.

As is clear from Table 16, the yield increase of from 104% to 115% was observed by the adding of from 0.25% to 0.025% xylooligosaccharide to the soil.

EXAMPLE 16

The callus of spinach was cultivated in a Murashige-Skoog culture medium at 150 r.p.m. for 2 weeks at 25° C. to provide 370 g of culture cells. The culture cells were dispersed in 2 liters of distilled water, treated by a ultrasonic crusher (Polytron) to crush the culture cells, and one liter of ethanol was added thereto to precipitate cell wall polysaccharide, whereby 15 g of cell wall polysaccharide was obtained.

After dissolving this polysaccharide in 300 ml distilled water and adjusting the pH of the solution to 5.1, 300 mg of Pectolyase Y-23, 750 mg of Doriselase, and 600 mg of Cellulase Onozuka R-10 were added to the solution and then the hydrolysis of the polysaccharide was performed for 4 hours at 25° C. After heating the reaction mixture to 100° C. for 10 minutes to inactivate the enzymes, the reaction mixture was passed through a column (5 cm×100 cm) packed with Biogel P-2 to provide 3.5 g of fraction containing oligosaccharides of biose to decanose.

The plant growth accelerating action of the oligosaccharide of the cell wall polysaccharide of the plant thus obtained was determined using cotyledons. That is, 36 grains of the seeds of Kaiware Daikon were placed on a synthetic resin mat set in a glass vessel and then, after adding 70 ml of tap water, the seeds were cultivated for 4 days in the dark at 23° C. and then for 2 days under the irradation condition of 5,000 lux. In this case, the oligosaccharide of the cell wall polysaccharide of the plant was added to the system at the indicated ratios of 2.5% to 0.000025% to the amount of the tap water.

The results obtained are shown in Table 17.

TABLE 17

| Added Amount of Oligosaccharide Obtained by Decomposing Cell Wall Polysaccharide of the Plant (%) | Stalk-Leave Length (%) | Root Length (%) |
| --- | --- | --- |
| 2.5 | 98 | 86 |
| 0.25 | 111 | 196 |
| 0.025 | 135 | 196 |
| 0.0025 | 121 | 289 |
| 0.00025 | 108 | 141 |
| 0.000025 | 101 | 98 |

The numeral values in Table 17 are the stalk-leaf length (cm) and the root length (cm) of each case with those of Kaiware Daikon cultivated without the oligosaccharide obtained by decomposing the cell wall polysaccharide of the plant being defined as 100.

EXAMPLE 17

One part by weight of seed of Kaiware Daikon was coated by spraying with 1 part by weight of the aqueous solutions containing 0.7 to 0.025% oligosaccharide obtained by decomposing the cell wall polysaccharide of plant the and 0.75% sodium alginate and dried in air stream of 40° C. to 50° C.

Then, 50 grains of the seeds coated with the oligosaccharide obtained by decomposing the cell wall polysaccharide of the plant obtained as described above were placed on a synthetic resin mat set in a glass vessel and, after adding thereto 70 ml of tap water, the seeds were cultivated for 4 days in the dark at 23° C. and for 2 days under irradiation of 5,000 lux.

For Control Group, the seeds without being coated were also cultivated under the same conditions as described above.

The results obtained are shown in Table 18.

The oligosaccharide obtained by decomposing the cell wall polysaccharide had been prepared by the same manner as in Example 16.

TABLE 18

| Coated Amount of Oligosaccharide obtained by decomposing cell wall polysaccharide of plant per grain of seed (γ) | Mean Stalk-Leaf Length (cm) | Mean Root Length (cm) |
| --- | --- | --- |
| 100 | 7.65 (115) | 8.64 (166) |
| 50 | 7.74 (117) | 8.58 (165) |
| 25 | 7.26 (109) | 7.59 (146) |
| 5 | 6.89 (104) | 6.43 (123) |
| 2.5 | 6.70 (101) | 5.35 (103) |
| 0 | 6.64 (100) | 5.21 (100) |

The numeral values in the parentheses are the values of each case with the means values of the Control Group being defined as 100.

As is clear from the above table, in the case of using the seeds coated with the oligosaccharide obtained by decomposing the cell wall polysaccharide of the plant at from 5γ to 100γ, the growth accelerating action of from 104% to 117% in stalk-leaf length and from 123% to 166% in root length was observed as compared with the seeds of the Control Group without being coated with the oligosaccharide.

EXAMPLE 18

After dissolving 20 g of polygalacturonic acid in one liter of water and adjusting the pH of the solution to 5.0, 200 mg of pectinase was added to the solution and the reaction was performed for 7 hours at 50° C. After the reaction was completed, the reaction mixture was heated to 100° C. for 15 minutes to inactive the enzyme and, after adding thereto 5 g of active carbon, the mixture was treated for 30 minutes. The reaction mixture was filtered and the filtrate obtained was concentrated to provide 123 ml of a solution containing 10% wt/vol polygalacuronic acid oligosaccharide.

The plant growth accelerating action of the polygalacturonic acid oligosaccharide thus obtained was determined using Kaiware Daikon. That is, 36 grains of the seeds of Kaiware Daikon were placed on a synthetic resin mat set in a glass vessle and, after adding thereto 70 ml of tap water, the seeds were cultivated for 4 days in the dark at 23° C. and then for 2 days under irradiation condition of 5,000 lux. In this case, the polygalacturonic acid oligosaccharide was added thereto at the indicated raio of from 2.5% to 0.000025% to the amount of the tap water.

The results obtained are shown in Table 19.

TABLE 19

| Added Amount of Polygalacuturonic Acid Oligosaccharide (%) | Stalk-Leaf Length (%) | Root Length (%) |
| --- | --- | --- |
| 2.5 | 96 | 98 |
| 0.25 | 111 | 148 |
| 0.025 | 106 | 159 |
| 0.0025 | 104 | 108 |
| 0.00025 | 102 | 104 |
| 0.000025 | 99 | 98 |
|  |  | (n = 36) |

The numeral values in Table 19 are the values (%) of the stalk-leaf length and the root length of each case with those of the Kaiware Daikon cultivated without the polygalacturonic acid oligosaccharide being 100%.

EXAMPLE 19

After dissolving 25 g of pectin in one liter of water and adjusting the pH of the solution to 5.0, 500 mg of pectinase was added to the solution and the reaction was performed for 23 hours at 50° C. After the reaction was completed, the reaction mixture was heated to 100° C. for 15 minutes to inactivate the enzyme and then treated with the addition of 5 g of active carbon for 30 minutes. The mixture was filtered and the filtrate obtained was concentrated to provide 165 ml of a solution containing 10% wt/vol pectin oligosaccharide.

The plant growth accelerating action of the pectin oligosaccharide thus obtained was determined using Kaiware Daikon. That is, 36 grains of the seeds of Kaiware Daikon were placed on a synthetic resin mat set in a glass vessel and, after adding thereto 70 ml of tap water, the seeds were cultivated for 4 days in the dark at 23° C. and then 2 days under irradiation of 5,000 lux. In this case, the pectin oligosaccharide was added thereto at the indicated ratios of from 2.5% to 0.000025% to the amount of the tap water. The results obtained are shown in Table 20.

TABLE 20

| Added Amount of Pectin Oligosaccharide (%) | Stalk-Leaf Length (%) | Root Length (%) |
|---|---|---|
| 2.5 | 86 | 91 |
| 0.25 | 116 | 149 |
| 0.025 | 107 | 121 |
| 0.0025 | 101 | 108 |
| 0.00025 | 103 | 101 |
| 0.000025 | 94 | 98 |
| | | (n = 36) |

The numeral values in Table 20 are the values (%) of the stalk-leaf length and the root length of each case with those of Kaiware Daikon cultivated without the pectin oligosaccharide being defined to be 100%.

EXAMPLE 20

After sowing 40 grains of the seeds of Chinese cabbage (breeding: Misugi cabbage) into 9 kg of black soil in a pot of 17 cm×60 cm×15 cm, the seeds were cultivated under natural conditions from June 15 to July 4. The experiment groups used were as follows.
Control Group:
Polygalacuronic acid oligo-saccharide is not added.
Added Group:
An aqueous solution of 22 g of polygalacturonic acid oligosaccharide dissolved in 3.6 liters of water was added to the black soil to form the soil containing 0.25% polygalacturonic acid to the amount of the black soil, and the cultivation was performed using the soil.

The polygalacturonic acid used had been prepared by the same manner as in Example 18.
The results obtained are shown in Table 21.

TABLE 21

| Experiment Group | Mean weight per stump of Chinese cabbage |
|---|---|
| Control Group | 4.9 ± 1.4 (100) |
| Added Group | 5.8 ± 1.3 (118) |

The numerical value in the parenthesis is the value (%) of the Added Group with the mean value of the Control Group being defined as 100%.

As is clear from Table 21, by the addition of the polygalacturonic acid oligosaccharide into the soil, the yield increase of 18% had been observed.

EXAMPLE 21

After dissolving 20 g of glucomannan in one liter of water and adjusting the pH of the solution to 5.0, 200 mg of a cellulase preparation having mannase activity (Meicelase, trade name, made by Meiji Seika Kaisha, Ltd.) was added to the solution and the reaction was completed, and 2 g of Baker's yeast was added to the reaction mixture and the reaction was performed for 24 hours at 25° C. To remove monosaccharides, the reaction product was decolored by the addition of 1% active carbon. The reaction mixture was filtered and the filtrate was concentrated to provide 120 ml of an aqueous solution containing 10% wt/vol glucomannan oligosaccharide.

The plant growth accelerating action of the glucomannan oligosaccharide thus obtained was determined using Kaiware Daikon. That is, 36 grains of the seeds of Kaiware Daikon were placed on a synthetic resin mat set in a glass vessel and after adding thereto 70 ml of tap water, the seeds were cultivated for 4 days in the dark at 23° C. and for 2 days under irradiation of 5,000 lux. In this case, glucomannan oligosaccharide was added thereto at the indicated ratios of 2.5% to 0.000025% to the amount of the tap water. The results obtained are shown in Table 22.

TABLE 22

| Added Amount of Pectin Oligosaccharide (%) | Stalk-Leaf Length (%) | Root Length (%) |
|---|---|---|
| 2.5 | 76 | 91 |
| 0.25 | 140 | 330 |
| 0.025 | 137 | 316 |
| 0.0025 | 112 | 254 |
| 0.00025 | 107 | 132 |
| 0.000025 | 98 | 101 |
| | | (n = 36) |

The numeral values in Table 22 are the values (%) of the stalk-leaf length and the root length of each case with those of the plant cultivated without the glucomannan oligosaccharide being defined to be 100.

As is clear from Table 22, by the addition of glucomannan oligosaccharide, the growth acceleration action of maximum 140% in stalk-leaf length and maximum 330% in root length was observed.

EXAMPLE 22

After placing 2 grains of the seeds of honewort (white stem honewort) on a synthetic resin mat of 4 cm×4 cm, the mat was immersed in a liquid fertilizer containing 0.15% Otsuka House #1 and 0.1% Otsuka House #2 and the seeds were cultivated for 10 days under irradiation of 5,00 lux to perform germination and nursing. Thereafter, the seedlings obtained were transplanted to a hydroponic cultivation apparatus and cultivated for 2.5 months under the conditions of 8,000 lux and 23° to 24° C. The experiment groups used were as follows.
Control Group:
After nursing with the liquid fertilizer containing no glucomannan oligosaccharide, the seedlings were also cultivated with the liquid fertilizer containing no glucomannan oligasaccharide.

Added Group:

After nursing with the liquid fertilizer containing 0.025% glucomannan oligosaccharide, the seedlings were cultivatd with the liquid fertilizer containing 0.025% glucomannan oligosaccharide.

The glucomannan oligosaccharide used had been prepared by the same manner as in Example 21. The test results obtained are shown in Table 23.

TABLE 23

| Experiment Group | Mean Stalk-leaf Length (cm) | Mean Root Length (cm) |
|---|---|---|
| Glucomannan oligo-saccharide-Added Group | 24.8 | 2.7 |
| Control Group | 20.8 | 1.8 |
|  | | (n = 20) |

EXAMPLE 23

After dissolving 30 g of agarose in 3 liters of water and adjusting the pH of the solution to 6.0, agarase was added to the solution at 40 units per gram of agarase and the reaction was performed for 72 hours at 40° C. After the reaction was completed, the reaction mixture was cooled to 1° to 5° C., allowed to stand for 24 hours to form precipiates, which were filtered off, and the filtrate thus obtained was concentrated and lyophilized to provide 18 g of agrooligosaccharide.

The plant growth accelerating action of the agarooligosaccharide thus obtained was determined using cotyledons. That is, 36 grains of the seed of Kaiware Daikon were placed on a synthetic resin mat set in a glass vessel after adding thereto 70 ml of tap water, the seeds were cultivated for 4 days in the dark at 23° C. and then for 2 days under irradiation of 5,000 lux. In this case, agarooligosaccharide was added thereto at the indicated ratios of from 2.5% to 0.0025% to the amount of the tap water. The results obtained are shown in Table 24.

TABLE 24

| Added Amount of Agaro-oligosaccharide (%) | Stalk-Leaf Length (%) | Root Length (%) |
|---|---|---|
| 2.5 | 86 | 92 |
| 0.25 | 109 | 145 |
| 0.025 | 111 | 169 |
| 0.0025 | 103 | 100 |
|  |  | (n = 36) |

The numeral values in Table 24 are the values (%) of the stalk-leaf length and the root length of Kaiware Daikon with those of cotyledons cultivated without the agarooligosaccharide being defined to be 100%.

As is clear from Table 24, the agarooligosaccharide accelerated the growth of the stalk-leaf and the root of the plant at addition concentrations of from 0.25% to 0.025%.

EXAMPLE 24

To 20 g of powdered cellulose (Avicell, trade name, made by Asahi Kasei Kogyo Co., Ltd.) were added 40 ml of hydrochloric acid and 40 ml of sulfuric acid and then the reaction was performed for 5 hours at 25° C. After the termination of reaction, the reaction mixture was neutralized with 30% aqueous sodium hydroxide and then subjected to a desalting treatment by column chromatography using a column packed with Biogel P-2. By this treatment, a fraction of cellooligosaccharide having a polymerization degree of from 2 to 10 was separated, concentrated, and then lyophilized to provide 7.5 g of cellooligosaccharide.

The plant growth accelerating action of the cellooligosaccharide thus obtained was determined using Kaiware Daikon. That is, 36 grains of the seeds of Kaiware Daikon were placed on a synthetic resin mat set in a glass vessel and, after adding thereto 70 ml of tap water, the seeds were cultivated for 4 days in the dark at 23° C. and then for 2 days under irradiation of 5,000 lux. In this case, cellooligosaccharide was added at the indicated ratios of from 2.5% to 0.0025% to the amount of the tap water. The results obtained are shown in Table 25 below.

TABLE 25

| Added Amount of Cello-oligosaccharide (%) | Stalk-Leaf Length (%) | Root Length (%) |
|---|---|---|
| 2.5 | 86 | 79 |
| 0.25 | 110 | 186 |
| 0.025 | 113 | 192 |
| 0.0025 | 102 | 101 |
|  |  | (n = 36) |

The numeral values in Table 25 are the values (%) of the stalk-leaf length and the root length of each case with those of the plant cultivated without the cellooligosaccharide being defined to be 100%.

As is clear from Table 25, the cellooligosaccharide accelerated the growth of the stalk-leaf and the root of the plant at the concentrations ranging from 0.25% to 0.025%.

EXAMPLE 25

After grinding 100 kg of the tuber of a girasol (Helianthus tuberosus L) by means of a grinder, 400 liters of water was added thereto to provide a suspension containing 20% solid components. Then, after adding thereto oxalic acid at the final concentration of 0.1N, the hydrolysis was performed for one hour at 60° C. The reaction mixture was neutralized with calcium carbonate, and filtered by a centrifugal separator or a filter press, followed by concentration and drying to provide 8.2 kg of a powder product.

The composition of the inulooligosaccharide thus prepared was mainly composed of $F_2$ to $F_6$ as shown in Table 26, wherein G represents glucose and F represents fructose.

TABLE 26

| Hydrolyzed Product | G, F | $F_2$ | $F_3$ | $F_4$ | $F_5$ | $F_6$ | $F_{7-10}$ |
|---|---|---|---|---|---|---|---|
| Content (%) | 33.2 | 19.2 | 13.0 | 9.8 | 7.8 | 5.6 | 11.4 |

By treating 50 g of the composition thus obtained by column chromatography using a column packed with Biogel P-2, 23 g of inulooligosaccharide having a polymerization degree of from 2 to 10 was obtained.

The plant growth accelerating action of the inulooligosaccharide thus obtained was determined using Kaiware Daikon. That is, 36 grains of the seeds of Kaiware Daikon were placed on a synthetic mat set in a glass vessel and after adding thereto 70 ml of tap water, the seeds were cultivated for 4 days in the dark at 23° C. and then for 2 days under irradiation of 5,000 lux. In this case, the inulooligosaccharide was added thereto at the indicated ratios of from 2.5% to 0.0025% to the amount of the tap water. The results obtained are shown in Table 27.

TABLE 27

| Added Amount of Inu-looligosaccharide (%) | Stalk-Leaf Length (%) | Root Length (%) |
| --- | --- | --- |
| 2.5 | 90 | 91 |
| 0.25 | 108 | 124 |
| 0.025 | 111 | 156 |
| 0.0025 | 100 | 103 |
|  |  | (n = 36) |

The values shown in Table 27 are the values (%) of the stalk-leaf length and the root length of each case with those of Kaiware Daikon cultivated without the inulooligosaccharide being defined to be 100%.

As is clear from Table 27, the inulooligosacharide accelerated the growth of the stalk-leaf and the root of the plant at the addition concentrations of from 0.25% to 0.025%.

EXAMPLE 26

After dissolving 20 g of mannan in 500 ml of hot water, 500 ml of 1N aqueous solution of hydrochloric acid was added to the solution and the hydrolysis was performed for 2 hours at 90° C. After the reaction was completed, the reaction mixture was neutralized to provide a decomposition product. The content of oligosaccharide having polymerization degree of from 2 to 10 in the decomposition product was 43%.

Then, the plant growth accelerating action of the mannan oligosaccharide thus obtained was determined using Kaiware Daikon. That is, 36 grains of the seeds of Kaiware Daikon were placed on a synthetic resin mat set in a glass vessel and after adding thereto 70 ml of tap water, the seeds were cultivated for 4 days in the dark at 23° C. and for 2 days under irradiation of 5,000 lux. In this case, the mannan oligosaccharide was added thereto at the indicated ratios of from 0.25% to 0.00025% to the amount of the tap water. The results obtained are shown in Table 28.

TABLE 28

| Added Amount of Mannan Oligosaccharide (%) | Stalk-Leaf Length (%) | Root Length (%) |
| --- | --- | --- |
| 0.25 | 114 | 189 |
| 0.025 | 121 | 241 |
| 0.0025 | 110 | 166 |
| 0.00025 | 102 | 104 |
|  |  | (n = 36) |

The numeral values in Table 28 are the values (%) of the stalk-leaf length and the root length of each case with those of Kaiware Daikon cultivated without the mannan oligosaccharide being defined to be 100%.

As is clear from Table 28, the mannan oligosaccharide accelerated the growth of the stalk-leaf and the root of the plant at the addition concentrations of from 0.25% to 0.025%.

EXAMPLE 27

After dissolving 20 g of fucoidin in 500 ml of hot water, 500 ml of 1N aqueous solution of hydrochloric acid was added to the solution and the hydrolysis of focoidin was performed for 2 hours at 90° C. When the reaction was completed, the reaction mixture was neutralized to provide a decomposition product. The oligosaccharide having a polymerization degree of from 2 to 10 in the decomposition product was 43%.

The plant growth accelerating action of the fucoidan oligosaccharide thus obtained was determined using Kaiware Daikon. That is, 36 grains of the seeds of Kaiware Daikon were placed on a synthetic resin mat set in a glass vessel and after adding thereto 70 ml of tap water, the seeds were cultivated for 4 days in the dark at 23° C. and then for 2 days under the iradiation condition of 5,000 lux. In this case, the fucoidin oligosaccharide was added at the indicated ratios of from 0.25% to 0.00025% to the amount of the city water. The results obtained are shown in Table 29.

TABLE 29

| Added Amount of Fucoidin Oligosaccharide (%) | Stalk-Leaf Length (%) | Root Length (%) |
| --- | --- | --- |
| 0.25 | 114 | 189 |
| 0.025 | 129 | 263 |
| 0.0025 | 109 | 143 |
| 0.00025 | 100 | 103 |
|  |  | (n = 36) |

The numeral values in Table 29 are the values (%) of the stalk-leaf length and root length of Kaiware Daikon of each case with those of octyledgns cultivated without the fucoidin oligosaccharide being defined to be 100%.

As is clear from Table 29, the fucoidin oligosaccharide accelerated the growth of the stalk-leaf and the root of the plant at the addition concentrations of from 0.25% to 0.0025%.

EXAMPLE 29

After dissolving 20 g of gum arabic in 500 ml of hot water, 500 ml of 1N aqueous hydrochloric acid solution was added thereto and the hydrolysis was performed for 2 hours at 90° C. After the reaction was completed, the reaction mixture was neutralized to provide a decomposition product. The content of the oligosaccharide having a polymerization degree of from 2 to 10 in the decomposition product was 34%.

The plant growth accelerating action of the gum arabic oligosaccharide thus obtained was determined using Kaiware Daikon. That is, 36 grains of the seeds of octyledons were placed on a synthetic resin mat set in a glass vessel and, after adding thereto 70 ml of tap water, the seeds were cultivated for 4 days in the dark at 23° C. and for 2 days under irradiation of 5,000 lux. In this case, the gum arabic oligosaccharide was added at the indicated ratios of from 0.25% to 0.00025% to the amount of city water. The results obtained are shown in Table 30.

TABLE 30

| Added Amount of Gum Arabic Oligosaccharide (%) | Stalk-Leaf Length (%) | Root Length (%) |
| --- | --- | --- |
| 0.25 | 110 | 141 |
| 0.025 | 114 | 189 |
| 0.0025 | 106 | 121 |
| 0.00025 | 98 | 100 |
|  |  | (n = 36) |

The numeral values in Table 30 are the values (%) of the stalk-leaf length and the root length of Kaiware Daikon in each case with those of octyledons cultivated without the gum arabic oligosaccharide being defined to be As is clear from Table 30, the gum arabic oligosaccharide accelerated the growth of the stalk-leaf and the root of the plant at the addition concentrations of from 0.25% to 0.0025%.

EXAMPLE 29

After dissolving 20 g of polyethylene glycol alginic acid in 500 ml of hot water, 500 ml of 1N aqueous 1N hydrochloric acid solution was added to the solution and the hydrolysis thereof was performed for 2 hours at 90° C. After the reaction was completed, the reaction mixture formed was neutralized to provide a decomposition product. The content of the oligosaccharide having polymerization degree of from 2 to 10 in the decomposition product was 58%.

The plant growth accelerating action of the polyethylene glycol alginic acid oligosaccharide thus obtained was determined using Kaiware Daikon. That is, 36 grains of the seeds of Kaiware Daikon were placed on a synthetic resin mat set in a glass vessel and after adding thereto 70 ml of tap water, the seeds were cultivated for 4 days in the dark at 23° C. and then 2 days under irradiation of 5,000 lux. In this case, the polyethylene glycol alginic acid oligosaccharide was added at the indicated ratios of from 0.25% to 0.00025% to the amount of the city water. The results obtained are shown in Table 31 below.

TABLE 31

| Added Amount of Polyethylene Glycol Alginic Acid Oligosaccharide (%) | Stalk-Leaf Length (%) | Root Length (%) |
|---|---|---|
| 0.25 | 108 | 146 |
| 0.025 | 114 | 206 |
| 0.0025 | 109 | 169 |
| 0.00025 | 101 | 98 |
| | | (n = 36) |

The neumeral values in Table 31 are the values (%) of the stalk-leaf length and the root length of Kaiware Daikon in each case with those of Kaiware Daikon cultivated without the polyethylene glycol alginic acid oligosaccharide being defined to be 100%.

As is clear from Table 31, the polyethylene glycol alginic acid oligosaccharide accelerated the stalk and root of the plant at the addition concentrations of from 0.25% to 0.0025%.

EXAMPLE 30

After dissolving 20 g of carrageenan in 500 ml of hot water, 500 ml of 1N aqueous hydrochloric acid solution was added to the solution and the hydrolysis thereof was performed for 2 hours at 90° C. After the reaction, was completed, the reaction mixture formed was neutralized to provide a decomposition product. The content of the oligosaccharide having a polymerization degree of from 2 to 10 in the decomposition product was The plant growth accelerating action of the carrageenan oligosaccharide thus obtained was determined using Kaiware Daikon. That is, 36 grains of the seeds of Kaiware Daikon were placed on a synthetic resin mat set in a glass vessel and after adding thereto 70 ml of tap water, the seeds were cultivated for 4 days in the dark at 23° C and then for 2 days under irradiation of 5,000 lux. In this case, the carrageenan oligosaccharide was added at the indicated ratios of from 0.25% to 0.00025% to the amount of the tap water. The results obtained are shown in Table 32.

TABLE 32

| Addition Amount of Carrageenan Oligo-saccharide (%) | Stalk-Leaf Length (%) | Root Length (%) |
|---|---|---|
| 0.25 | 105 | 124 |
| 0.025 | 110 | 181 |
| 0.0025 | 106 | 141 |
| 0.00025 | 94 | 98 |
| | | (n = 36) |

The numeral values in Table 32 are the values (%) of the stalk-leaf length and the root length of Kaiware Daikon in each case with those of Kaiware Daikon cultivated without the carrageenan oligosaccharide being defined to be 100%.

As is clear from Table 32, the carrageenan oligosaccharide accelerated the growth of the stalk-leaf and the root of the plant at the addition concentrations of from 0.25% to 0.0025%.

EXAMPLE 31

*Azotobacter vinelandii* IAM 1078 was subjected to shaking culture in 30 ml of a liquid culture medium placed in an Erlenmeyer flask (sterilized for 15 min. at 120° C.) and containing 0.025% $KH_2PO_4$, 0.0005% $Na_2MoO_4 \cdot 2H_2O$, 0.0125% $MgSO_4 \cdot 7H_2O$, 0.0005% $MnSO_4 \cdot 4H_2O$, 0.025% NaCl, 0.0005% $FeSO_4 \cdot 7H_2O$, and 2.0% sucrose for 72 hours at 240 rpm and 30° C. to provide a seed culture solution.

Then, 400 ml of the culture medium having the aforesaid composition was placed in a one liter Erlenmeyer flask, and after sterilizing by an ordinary method for 30 minutes at 120° C., 20 ml of the seed culture solution prepared above was added thereto, and the cultivation was performed at 240 rpm for 5 days at 30° C. After adding 2 liters of water to 2 liters of the culture liquid thus obtained, the mixture was subjected to centrifugal separation for 40 minutes at 10,000 G, wherby 1.9 liters of a supernatant liquid was obtained. The liquid was concentrated to 300 ml, and ethanol was added thereto to precipitate polysaccharide, which was collected by centrifugal separation to provide 1.2 g of polysaccharide.

To the polysaccharide thus obtained was added 1.2 liters of water to form 0.1% aqueous solution thereof, hydrochloric acid was added to the solution at a final concentration of 0.1N, and, after performing the hydrolysis for 6 hours at 100° C., the reaction mixture obtained was neutralized with sodium hydroxide to provide the desired decomposition product.

The decomposition product thus obtained was concentrated to 20 ml, desalted by column chromatography using a column packed with Sephadex G25, and a fraction containing the oligosaccharide having a polymerization degree of from 2 to 20 was collected, concentrated, and lyophilized to provide 420 mg of oligosaccahride.

The plant growth accelerating action of the oligosaccahride thus obtained and also the polysaccharide before decomposition was determined using Kaiware Daikon. 36 grains of the seeds of Kaiware Daikon were placed on a synthetic resin mat set in a glass vessel and after adding thereto 70 ml of tap water, the seeds were cultivated for 4 days in the dark at 23° C. and for 2 days under irradiation of 5,000 lux. In this case, the oligosaccharide, etc., was added thereto each at the indicated concentrations of from 0.025% to 0.00025%. The results obtained are shown in Table 33.

TABLE 33

| Sample | Added Amount (%) | Stalk-Leaf Length (%) | Root Length (%) |
|---|---|---|---|
| A | 0.025 | 138 | 265 |
| A | 0.0025 | 121 | 248 |
| A | 0.00025 | 113 | 185 |
| B | 0.025 | 98 | 100 |
| Control | 0 | 100 | 100 |
|  |  |  | (n = 36) |

A: Oligosaccharide obtained by decomposing polysaccharide of *Azotobacter vinelandii*.
B: Polysaccharide produced by *Azotobacter vinelandii*.

The numeral values in Table 33 are the values (%) of the stalk-leaf length and the root length of Kaiware Daikon in each case with those of Kaiware Daikon cultivated without the oligosaccharide or polysaccharide being defined to be 100%.

EXAMPLE 32

In a pot of 17 cm×60 cm×15 cm was placed 9 kg of black soil and after sowing 40 grains of the seeds of Chinese cabbage (breeding: Misugi cabbage) into the soil, the seeds were cultivated for 30 days under natural conditions. The experiment groups used were as follows.
Control Group:
 Oligosaccharide is not added.
Added Group:
 An aqueous solution of 2.2 g of the oligosaccharide in 3.6 liters of water was added to the black soil at a concentration of 0.025% to the amount of the soil and the cultivation was performed.

In addition, the oligosaccharide used had been prepared from 10 liters of the culture liquid as described in Example 31. The results obtained are shown in Table 34.

TABLE 34

| Experiment Group | Mean Value per Stump of Chinese Cabbage |
|---|---|
| Control Group | 4.8 ± 1.5 (100) |
| 0.025% Added Group | 5.2 ± 1.4 (108) |

The numeral value in the parenthesis is the value with the mean value of Control Group being defined to be 100%.

As is clear from the above table, by the addition of the oligasaccharide into the soil, the yield increase of 8% was observed.

EXAMPLE 33

In a 250 ml Erlenmeyer flask was placed 30 ml of a culture medium containing 1.0% mannitol, 0.1% $MgCl_2$, 0.1% sodium glutamate, 0.1% $K_2HPO_4$, 0.02% $MgSO_4 \cdot 7H_2O$, 0.004% $CaCl_2$, and 10γ of biotin, 100γ of thiamine, 2.5 mg of $FeCl_3 \cdot 6H_2O$, 0.01 mg of $H_3BO_3$, 0.01 mg of $ZnSO_4 \cdot 7H_2O$, 0.01 mg of $CoCl_2 \cdot 7H_2O$, 0.1 mg of $CuSO_4 \cdot 5H_2O$, and 0.01 mg of $Na_2MoO_4 \cdot 2H_2O$ per liter of the culture medium as minor nutrients and after sterilizing the culture medium for 15 minutes at 120° C., *Agrobacterium timefaciens* IAM 1037 was cultivated in the culture medium at 240 rpm for 3 days at 25° C. to provide the 1st seed culture solution.

Also, 300 ml of the aforesaid culture medium was placed in a one liter Erlenmeyer flask and after sterilizing the culture medium for 15 minutes at 120° C., 10 ml of the 1st seed culture solution obtained above was added thereto and cultivated at 240 rpm for 3 days at 25° C. to provide the 2nd seed culture solution.

Then, 20 liters of the culture medium having the same composition as above was charged in an 30-liter jar fermenter and after sterilizing the culture medium for 30 minutes at 120° C., 100 ml of the 2nd seed culture solution was inoculated to the medium and cultivated at 200 rpm for 6 days at 25° C. After adding 20 liters of water to 20 liters of the culture liquid, the mixture was subjected to centrifugal separation for 30 minutes at 10,000 G to remove the cells, the supernatant liquid was concentrated to 4 liters, and 10 liters of ethanol was added thereto to precipitate polysaccharide, which was separated by centrifugal separation and dried to provide 24 g of polysaccharide.

After dissolving 10 g of the polysaccharide in 10 liters of water, hydrochloric acid was added thereto at final concentration of 0.1N, the hydrolysis was performed for 6 hours at 100° C., and then the reaction mixture obtained was neutralized with sodium hydroxide. Thereafter, the reaction mixture was concentrated to 100 ml and subjected to the treatment by a column packed with Sephadex G25 to perform desalting and also obtain a fraction containing oligosaccharide having a polymerization degree of from 2 to 20. The fraction was concentrated and lyophilized to provide 3.4 g of the desired product.

The plant growth acceleration action of the oligosaccharide thus obtained and of the polysaccharide before decomposition was determined using Kaiware Daikon. 36 grains of the seeds of Kaiware Daikon were placed on a synthetic resin mat set in a glass vessel and after adding thereto 70 ml of tap water, the seeds were cultivated for 4 days in the dark at 23° C. and for 2 days under irradiation of 5,000 lux. In this case, the oligosaccharide, etc., was added thereto at the indicated ratios of from 0.025% to 0.00025% to the amount of the tap water. The results obtained are shown in Table 35.

TABLE 35

| Sample | Added Amount (%) | Stalk-Leaf Length (%) | Root Length (%) |
|---|---|---|---|
| A | 0.025 | 110 | 214 |
| A | 0.010 | 112 | 245 |
| A | 0.005 | 100 | 181 |
| A | 0.0025 | 98 | 121 |
| A | 0.00025 | 102 | 108 |
| B | 0.025 | 100 | 101 |
| Control | 0 | 100 | 100 |
|  |  |  | (n = 36) |

A: Oligosaccharide obtained by decomposing the polysaccharide produced by *Agrobacterium tumefaciens*.
B: Polysaccharide produced by *Agrobacterium tumefaciens*.

The numeral values in Table 35 are the values (%) of the stalk-leaf length and the root length of cotyledons in each case with those of cotyledon cultivated without the oligosaccharide and the polysaccharide.

EXAMPLE 34

In a pot of 17 cm×60 cm×15 cm was placed 9 kg of black soil and 40 grains of the seeds of Chinese cabbage (breeding: Misugi cabbage) were sown into the soil and cultivated for 30 days under natural conditions. The experiment groups used were as follows.

Control Group:
Oligosaccharide is not added.
Added Group:
An aqueous solution of 11 g or 2.2 g of oligosaccharide in 3.6 liters of water was added to the black soil at 0.125% or 0.025% thereof to the amount of the soil and the cultivation was performed using the soil.

The oligosaccharide used in the test had been prepared from 40 liters of the culture liquid obtained by the same manner as in Example 33.

The results obtained are shown in Table 36.

TABLE 36

| Experiment Group | Mean Weight per Stump of Chinese Cabbage (g) |
| --- | --- |
| Control Group | 4.9 ± 1.4 (100) |
| 0.125% Added Group | 5.4 ± 1.5 (110) |
| 0.025% Added Group | 5.1 ± 1.5 (104) |
| | (n = 40) |

The numeral values shown in the parentheses are the values (%) of each case with the mean value of the Control Group being defined to 100%.

Aa is clear from the above table, by adding the oligosaccharide to the soil at 0.125% to 0.025%, the yield increase of from 4% to 10% was observed.

EXAMPLE 35

In a 250 milliliter Erlenmeyer flask was placed a culture medium containing 1.0% mannitol, 0.1% $MgCl_2$, 0.1% sodium glutamate, 0.1% $K_2HPO_4$, 0.02% $MgSO_4 \cdot 7H_2O$, 0.004% $CaCl_2$, and 10γ of biotin, 100γ of thiamine, 2.5 mg of $FeCl_3 \cdot 6H_2O$, 0.01 mg of $H_3BO_3$, 0.01 mg of $ZnSO_4 \cdot 7H_2O$, 0.01 mg of $cocl_2 \cdot 7H_2O$, 0.01 mg of $CuSO_4 \cdot 5H_2O$, and 0.01 mg of $Na_2MoO_4 \cdot 2H_2O$ per liter of the culture medium as minor nutrients and after sterilizing the culture medium for 15 minutes at 120° C., *Rhyzobium meliloti* IAM 12611 was inoculated and cultivated at 240 rpm for 3 months at 25° C. to provide a 1st seed culture solution.

Also, 300 ml of the culture medium having the same composition as above was placed in a one liter Erlenmeyer flask and after sterilizing the medium for 15 minutes at 120° C., the 1st seed culture solution described above was inoculated and cultivated at 240 rpm for 3 days at 25° C. to provide the 2nd seed culture solution.

Furthermore, 20 liters of the culture medium having the same composition as above was charged in a 30 liter jar fermenter and after sterilizing the medium for 30 minutes at 120° C., 100 ml of the 2nd seed culture solution was inoculated and cultivated at 200 rpm for 6 days at 25° C. Then, 20 liters of water was added to 20 liters of the culture liquid obtained, the mixture was subjected to centrifugal separation for 30 minutes at 10,000 G to remove the cells, the supernatant liquid formed was concentrated to 4 liters, and 10 liters of ethanol was added thereto to precipitate polysaccharide, which was separated by centrifugal separation and dried to provide 12 g of polysaccharide.

After dissolving 10 g of the polysaccharide thus obtained in 10 liters of water, hydrochloric acid was added thereto at a final concentration of 0.1N and the hydrolysis was performed for 6 hours at 100° C. Then, the reaction mixture obtained was neutralized with sodium hydroxide, concentrated to 200 ml, and subjected to a treatment using a column packed with Sephadex G-25 to perform desalting and to obtain a fraction of an oligosaccharide having a polymerization degree of from 2 to 20. The fraction was concentrated and lyophilized to provide 4.8 g of the desired product.

The plant growth accelerating action of the oligosaccharide thus obtained and the polysaccharide before decompoasition was determined using Kaiware Daikon. 36 grains of the seeds of Kaiware Daikon were placed on a synthetic resin mat set in a glass vessel and after adding thereto 70 ml of tap water, the seeds were cultivated for 4 days in the dark at 23° C. and then for 2 days under irradiation of 5,000 lux. In this case, the oligosaccharide, etc., was added thereto at the indicated ratios of from 0.025% to 0.00025% to the amount of the city water. The results obtained are shown in Table 37.

TABLE 37

| Sample | Added Amount (%) | Stalk-Leaf Length (%) | Root Length (%) |
| --- | --- | --- | --- |
| A | 0.025 | 102 | 119 |
| A | 0.010 | 108 | 195 |
| A | 0.005 | 110 | 171 |
| A | 0.0025 | 100 | 168 |
| A | 0.00025 | 101 | 261 |
| B | 0.025 | 98 | 97 |
| Control | 0 | 100 | 100 |
| | | | (n = 36) |

A: Oligosaccharide obtained by decomposing the polysaccharide produced by *Rhyzobium meliloti*.
B: Polysaccharide produced by *Rhyzobium meliloti*.

The numeral values in Table 37 are the values (%) of the stalk-leaf length and the root length of Kaiware Daikon in each case with those of Kaiware Daikon cultivated without the oligosaccharide and the polysaccharide.

EXAMPLE 36

In a pot of 17 cm×60 cm×15 cm was placed 9 kg of black soil and 40 grams of the seeds of Chinese cabbage (breeding: Misugi cabbage) were sown into the soil and cultivated for 30 days under natural conditions. The experiment Groups used were as follows.
Control Group:
Oligosaccharide is not added.
Added Group:
An aqueous solution of 22 g or 2.2 g of oligosaccharide in 3.6 liters of water was added to the black soil at 0.25% or 0.025% thereof to the amount of the soil and the cultivation was performed using the soil.

The oligosaccharide used had been prepared from 40 liters of the culture liquid according to the method described in Example 35 followed by hydrolysis with hydrochloric acid and neutralization.

The results are shown in Table 38.

TABLE 38

| Experiment Group | Mean Weight per Stump of Chinese Cabbage |
| --- | --- |
| Control Group | 4.6 ± 1.6 (100) |
| 0.125% Added Group | 5.1 ± 1.4 (111) |
| 0.025% Added Group | 5.0 ± 1.7 (109) |
| | (n = 40) |

The numeral values in the parentheses are the values of each case with the mean value of the Control Group being defined to be 100%.

As is clear from the above table, by the addition of the oligosaccharide to the soil at 0.25% or 0.025%, the yield increase of from 9% to 11% was observed.

EXAMPLE 37

In a 250 ml Erlenmeyer flask was placed 30 ml of a culture medium containing 1% lactose, 0.5% peptone, 0.1% $KH_2PO_4$, 0.05% $MgSO_4 \cdot 7H_2O$, and 0.0033% Rose Bengale, and after sterilizing the culture medium for 15 minutes at 120° C., Enterobacter cloacae FERM-8968 was inoculated in an amount of one platinum loop and cultivated at 240 rpm for 24 hours at 30° C. to provide the 1st seed culture solution.

Then, 300 ml of the culture medium having the composition as described above was placed in a one liter Erlenmeyer flask after sterilizing for 15 minutes at 120° C., and 10 ml of the 1st seed culture solution was inoculated thereto and cultivated at 240 rpm for 24 hours at 30° C. to provide the 2nd seed culture solution.

Also, 20 liters of the culture medium having the same composition as above was placed in a 30 liter jar fermenter and after sterilizing for 30 minutes at 120° C., 100 ml of the 2nd seed culture solution was inoculated and cultivated at 240 rpm for 2 days at 30° C.

Then, 20 liters of water was added to 20 liters of the culture liquid thus obtained, the mixture was subjected to centrifugal separation for 40 minutes at 10,000 G to remove the cells, the supernatant liquid formed was concentrated to 3 liters, and 7 liters of ethanol was added to the concentrate to precipitate polysaccharide, which was separated by centrifugal separation and dried to give 16 g of a polysaccharide.

After dissolving 10 g of the polysaccharide in 1 liter of water, hydrochloric acid was added to the solution at a final concentration of 0.1N, the hydrolysis was performed for 4 hours at 100° C., and the reaction mixture formed was neutralized with sodium hydroxide. Thereafter, the reaction mixture was concentrated to 100 ml and treated by a column packed with Sephadex G-25, whereby desalting was practiced and also a fraction of oligosaccharide having a polymerization degree of from 2 to 20 was recovered. The fraction was, then, concentrated and lyophilized to provide 4.2 g of the desired product.

The plant growth accelerating action of the oligosaccharide thus obtained and of the polysaccharide before decomposition was determined using Kaiware Daikon. That is, 36 grains of the seeds of Kaiware Daikon were placed on a synthetic resin mat set in a glass vessel and after adding thereto 70 ml of tap water, the seeds were cultivated for 4 days in the dark at 23° C. and then for 2 days under irradiation of 5,000 lux. In this case, the oligosaccharide, etc., was added at the indicated ratios of from 0.025% to 0.00025% to the amount of the city water. The results obtained are shown in Table 39.

TABLE 39

| Sample | Added Amount (%) | Stalk-Leaf Length (%) | Root Length (%) |
|---|---|---|---|
| A | 0.025 | 116 | 206 |
| A | 0.010 | 121 | 198 |
| A | 0.005 | 119 | 185 |
| A | 0.0025 | 118 | 169 |
| A | 0.00025 | 113 | 168 |
| B | 0.025 | 114 | 196 |
| B | 0.010 | 114 | 184 |

TABLE 39-continued

| Sample | Added Amount (%) | Stalk-Leaf Length (%) | Root Length (%) |
|---|---|---|---|
| B | 0.005 | 110 | 169 |
| B | 0.0025 | 110 | 144 |
| B | 0.00025 | 103 | 101 |
| | | | (n = 36) |

A: Oligosaccharide obtained by decomposing the polysaccharide produced by Enterobacter cloacae
B: Polysaccharide produced by Enterobacter cloacae The numeral values in Table 39 are the values (%) of the stalk-leaf length and the root length of Kaiware Daikon in each case with those of Kaiware Daikon cultivated without the oligosaccharide and the polysaccharide.

As is clear from the results shown in Table 39, the oligosaccharide obtained by decompositing the polysaccharide produced by Enterobacter cloacae showed the growth accelerating action for the plant at the added amount of from 0.025% to 0.00025%.

On the other hand, the polysaccharide produced by Enterobacter cloacae showed the growth accelerating action at 0.025% to 0.0025%.

EXAMPLE 38

In a pot of 17 cm×60 cm×15 cm was placed 9 kg of black soil and 40 grains of the seed of Chinese cabbage (breeding: Misugi cabbage) were sowed into the soil and cultivated for 30 days under natural conditions. The experiment groups used were as follows.
Control Group:
  Oligosaccharide is not added.
Leaf-Surface Applied Group:
  An aqueous solution of 160 mg or 16 mg of the oligosaccharide in 80 ml of water was applied to leaf-surfaces of Chinese cabbage every 7 days during cultivation.

The oligosaccharide used had been prepared by the same manner as in Example 37. The results obtained are shown in Table 40.

TABLE 40

| Experiment Group | Mean Weight per Stump of Chinese Cabbage |
|---|---|
| Control Group | 4.9 ± 1.4 (100) |
| Leaf-Surface Applied Group (4 mg/stump) | 7.3 ± 1.4 (149) |
| Leaf-Surface Applied Group (0.4 mg/stump) | 7.1 ± 1.5 (145) |
| | (n = 40) |

The numeral values in the parentheses are the values (%) of each case with the mean value of the Control Group being defined to be 100%.

As is clear from the above table, by applying the oligosaccharide to the leaf surfaces of Chinese cabbage at a rate of from 0.4 mg or 4.0 mg per stump thereof, the yield increase of from 45% to 49% was obtained.

EXAMPLE 39

After dissolving 1 g of a polysaccharide (made by Sigma Co.) produced by Zoogloea ramigera in 1 liter of water, hydrochloric acid was added to the solution at a final concentration of 0.1N and after hydrolyzing the polysaccharide for 4 hours at 100° C., the reaction mixture obtained was neutralized with sodium hydroxide. The solution containing the decomposed product thus obtained was concentrated to 50 ml and passed through a column packed with Sephadex G-25 to perform desalting and also recover a fraction containing oligosaccharide having a polymerization degree of from 10 to 20. The fraction was concentrated and lyophilized to provide 320 mg of oligosaccharide.

The plant growth accelerating action of the oligosaccharide thus obtained and of the polysaccharide before decomposition was determined using Kaiware Daikon. That is, 36 grains of the seeds of Kaiware Daikon were placed on a synthetic resin mat set in a glass vessel and after adding thereto 70 ml of tap water, the seeds were cultivated for 4 days in the dark at 23° C. and then for 2 days under irradiation of 5,000 lux. In this case, oligosaccharide, etc., was added thereto at the indicated ratios of from 0.025% to 0.00025% to the amount of the tap water. The results obtained are shown in Table 41.

TABLE 41

| Sample | Added Amount (%) | Stalk-Leaf Length (%) | Root Length (%) |
|---|---|---|---|
| A | 0.025 | 120 | 263 |
| A | 0.010 | 109 | 240 |
| A | 0.005 | 110 | 201 |
| A | 0.0025 | 111 | 186 |
| A | 0.00025 | 100 | 131 |
| B | 0.025 | 100 | 101 |
| Control | 0 | 100 | 100 |
| | | | (n = 36) |

A: Oligosaccharide obtained by decomposing the polysaccharide produced by *Zoogloea ramigera*.
B: Polysaccharide produced by *Zoogloea ramigera*.

The numeral values in Table 40 are the values (%) of the Stalk-leaf length and the root length of Kaiware Daikon in each case with those of Kaiware Daikon cultivated without the oligosaccharide, etc.

EXAMPLE 40

After dissolving 50 g of Xanthan Gum (made by Sigma Co.), a commercially available polysaccharide produced by migroorganisms belonging to genus Xanthomonas, in liters of water, hydrochloric acid was added to the solution at a final concentration of 0.1N and after performing the hydrolysis for 7 hours at 100° C., the reaction mixture was neturalized with sodium hydroxide. Then, the solution containing the decomposed product thus obtained was concentrated to 500 ml and passed though a column packed with Sephadex G-25 to perform desalting and also to recover a fraction containing oligosaccharide having a polymerization degree of from 2 to 20. The fraction was concentrated and lyophilized to provide 21 g of oligosaccharide.

The plant growth accelerating action of the oligosaccharide thus obtained and of the polysaccharide before decomposition was determined using Kaiware Daikon. 36 grains of the seeds of cotyledons were placed on a synthetic resin mat set in a glass vessel and after adding thereto 70 ml of tap water, the seeds were cultivated for 4 days in the dark at 23° C. and then for 2 days under irradiation of 5,000 lux. In this case, the oligosaccharide, etc., was added thereto at the indicated ratios of from 0.025% to 0.00025% to the amount of the tap water. The results obtained were as shown in Table 42.

TABLE 42

| Sample | Added Amount (%) | Stalk-Leaf Length (%) | Root Length (%) |
|---|---|---|---|
| A | 0.025 | 113 | 216 |
| A | 0.010 | 107 | 126 |
| A | 0.005 | 105 | 192 |
| A | 0.0025 | 105 | 143 |
| A | 0.00025 | 98 | 101 |
| B | 0.025 | 99 | 98 |
| Control | 0 | 100 | 100 |
| | | | (n = 36) |

A: Oligosaccharide obtained by decomposing Xanthan Gum.
B: Xanthan Gum.

The numeral values shown in Table 41 are the values (%) of the stalk-leaf length and the root length of Kaiware Daikon in each case with those of Kaiware Daikon cultivated without the oligosaccharide, etc.

EXAMPLE 41

In a pot of 17 cm×60 cm×15 cm was placed 9 kg of black soil and 40 grains of the seed of Chinese cabbage (breeding: Misugi cabbage) were sowed into the soil and cultivated for 30 days under natural conditions. The experiment groups used were as follows.

Control Group:
Oligosaccharide is not added.

Added Group:
An aqueous solution of 2.2 g of oligosaccharide in 3.6 liters of water was added to the black soil at 0.025% thereof to the soil and the cultivation was performed using the soil.

The oligosaccharide used had been prepared by the same manner as in Example 40. The results obtained are shown in Table 43.

TABLE 43

| Experiment Group | Mean Weight per Stump of Chinese Cabbage |
|---|---|
| Control Group | 4.8 ± 1.3 (100) |
| 0.025% Added Group | 5.0 ± 1.4 (104) |
| | (n = 40) |

The numeral value in the parenthesis is the value (%) with the mean value of the Control Group being defined to be 100%.

As is clear from the above table, by the addition of the oligosaccharide to the soil at 0.025%, the yield increase of 4% was obtained.

EXAMPLE 42

After dissolving 10 g of Gellan Gum (made by Sanei Kagaku Kogyo K.K.), a commercially available polysaccharide produced by *Pseudomonas elodea*, in 10 liters of water, hydrochloric acid was added to the solution at a final concentration of 1.0N and after performing the hydrolysis for 15 minutes at 120° C., the reaction mixture was neutralized with sodium hydroxide. Then the solution containing the decomposition product thus obtained was concentrated to 1000 ml and passed through a column packed with Sephadex G-25 to perform desalting and also to recover a fraction containing oligosaccharide having a polymerization degree of from 2 to 20. The fraction was concentrated and dried to give 1.3 g of the oligosacchariděo The plant growth accelerating action of the oligosaccharide thus obtained was determined using Kaiware Daikon. 36 grains of the seeds of Kaiware Daikon were placed on a synthetic resin mat set in a glass vessel and after adding thereto 70 ml of tap water, the seeds were cultivated for 4 days in the dark at 23° C. and then for 2 days under irradiation of 5,000 lux. In this case, the oligosaccahride was added thereto at the indicated ratios of from 0.025% to 0.00025% to the amount of the tap water. Also, the experiment of adding Geran Gum to the black soil at 0.025% was performed by the same manner as above. The results obtained are shown in Table 44.

TABLE 44

| Added Amount (%) | Stalk-Leaf Length (%) | Root Length (%) |
| --- | --- | --- |
| Oligosaccharide | | |
| 0.025 | 136 | 306 |
| 0.0025 | 121 | 254 |
| 0.00025 | 116 | 231 |
| Geran Gum | | |
| 0.025 | 102 | 114 |
| 0.00025 | 98 | 101 |
| Control | | |
| 0 | 100 | 100 |
| | | (n = 36) |

The numeral values in Table 44 are the values (%) of the stalk-leaf length and the root length of Kaiware Daikon in each case with those of the mean values of Kaiware Daikon cultivated without the oligosaccharide, etc. being defined to be 100%.

EXAMPLE 43

After dissolving 1 g of Nigeran, a commercially available polysaccahride produced by *Aspergillus niger*, in liter of water, hydrochloric acid was added to the solution at a final concentration of 0.1N and after performing the hydrolysis for 4 hours at 100° C. the reaction mixture obtained was neutralized with sodium hydroxide. The solution containing the decomposition product thus obtained was concentrated to 50 ml and passed through a column packed with Sephadex G-25 to perform desalting and also to recover a fraction containing ologosaccharide having a polymerization degree of from 2 to 20. The fraction was concentrated and dried to provide 410 mg of the oligosaccharide.

The plant growth accelerating action of the oligosaccharide thus obtained and of the polysaccharide before decomposition was determined using Kaiwre Daikon. That is, 36 grains of the seeds of Kaiware Daikon were placed on a synthetic resin mat set in a glass vessel and after adding thereto 70 ml of tap water, the seeds were cultivated for 4 days in the dark at 23° C. and for 2 days under irradiation of 5,000 lux. In this case, the oligosaccharide, etc., was added thereto at the indicated ratios of from 0.025% to 0.00025% to the amount of the tap water. The results obtained are shown in Table 45.

TABLE 45

| Sample | Added Amount (%) | Stalk-Leaf Length (%) | Root Length (%) |
| --- | --- | --- | --- |
| A | 0.025 | 106 | 198 |
| A | 0.010 | 102 | 165 |

TABLE 45-continued

| Sample | Added Amount (%) | Stalk-Leaf Length (%) | Root Length (%) |
| --- | --- | --- | --- |
| A | 0.005 | 99 | 115 |
| A | 0.0025 | 100 | 111 |
| A | 0.00025 | 98 | 103 |
| B | 0.025 | 100 | 101 |
| Control | 0 | 100 | 100 |
| | | | (n = 36) |

A: Oligosaccharide obtained by decomposing Nigeran.
B: Nigeran.

The numerals shown in Table 45 are the values (%) of the stalk-leaf length and the root length of Kaiware Daikon in each case with those of the control being defined to be 100%.

EXAMPLE 44

After dissolving 100 mg of Mannan, a commercially available polysaccharide produced by *Saccharomyces cerevisiae*, in 100 ml of water, hydrochloric acid was added to the solution at a final concentration of 0.1N and after performing the hydrolysis for 6 hours at 100° C., the reaction mixture obtained was neutralized with sodium hydroxide. The solution containing the decomposition product thus obtained was concentrated to 10 ml and passed through a column packed with Sephadex G-25 to perform desalting and also to collect a fraction containing oligosaccharide having a polymerization degree of from 2 to 20. The fraction was concentrated and dried to give 36 mg of the oligosaccharide.

The plant growth accelerating action of the oligosaccharide thus obtained and the polysaccharide before decomposition was determined using Kaiware Daikon. 36 grains of the seeds of Kaiware Daikon were placed on a synthetic resin mat set in a glass vessel and after adding thereto 70 ml of city water, the seeds were cultivated for 4 days in the dark at 23° C. and for 2 days under irradiation of 5,000 lux. In this case, the oligosaccharide, etc., was added thereto at the indicated ratios of from 0.025% to 0.00025% to the amount of the tap water. The results obtained are shown in Table 46.

TABLE 46

| Sample | Added Amount (%) | Stalk-Leaf Length (%) | Root Length (%) |
| --- | --- | --- | --- |
| A | 0.025 | 121 | 360 |
| A | 0.010 | 118 | 289 |
| A | 0.005 | 110 | 204 |
| A | 0.0025 | 108 | 196 |
| A | 0.00025 | 99 | 143 |
| B | 0.025 | 99 | 102 |
| Control | 0 | 100 | 100 |
| | | | (n = 36) |

A: Oligosaccharide obtained by decomposing Mannan produced by *Saccharomyces cerevisiae*.
B: *Saccharomyces cereviae*.

The numeral values in Table 46 are the values (%) of the stalk-leaf length and the root length of Kaiware Daikon in each case with those of Kaiware Daikon of the control being defined to be 100%.

EXAMPLE 45

Seeds of Kaiware Daikon coated with oligosaccharide at the indicated ratios of from 2.5γ to 100γ per grain of the seed thereof were prepared by spraying one part by weight of an aqueous solution containing from 0.7% to 0.025% the oligosaccharide obtained by decomposing the polysaccharide produced *Enterobacter cloacae* FERM BP-1529 by the method as described in Example 37 and 0.75% sodium alginate onto one part by weight of the seeds of Kaiware Daikon and drying the seeds in an air stream at 40° C. to 50° C.

Then, 50 grains of the oligosaccahride-coated seeds thus obtained were placed on a synthetic resin mat set in a glass mat and after adding thereto 70 ml of tap water, the seeds were cultivated for 4 days in the dark at 23° C. and then for 2 days under irradiation of 5,000 lux.

For control, seeds of cotyledons without being coated were cultivated under the same manner as above. The results obtained are shown in Table 47.

TABLE 47

| Coated Amount of Oligosaccharide per Seed Grain ($\gamma$) | Mean Stalk-Leaf Length (cm) | Mean Root Length (cm) |
| --- | --- | --- |
| 100 | 8.71 (131) | 12.2 (243) |
| 50 | 8.37 (126) | 10.8 (208) |
| 25 | 7.97 (120) | 8.59 (165) |
| 5 | 7.17 (108) | 6.83 (131) |
| 2.5 | 6.71 (101) | 5.43 (104) |
| Control | 6.64 (100) | 5.21 (100) |
|  |  | (n = 25) |

The numeral values in the parentheses are the values (%) of each case with the mean values of the contrast being defined to be 100%.

As is clear from Table 46, in the case of using the seeds coated with the oligosaccharide at 5$\gamma$ to 100$\gamma$ per seed grain, the growth accelerating action of 108 to 131% in stalk-leaf length and 131 to 243% in root length was observed as compared with the case of using the seeds without being coated with the oligosaccharide.

While the invention has been described in detail and with reference to specific embodiments thereof, it will be apparent to one skilled in the art that various changes and modifications can be made therein without departing from the spirit and scope thereof.

What is claimed is:

1. A method of accelerating growth of a plant which comprises applying to the plant, the seeds of the plant or the locus of the plant a plant growth accelerating amount of a plant growth accelerating oligosaccharide, wherein the plant growth accelerating oligosaccharide is alginic acid oligosaccharide, inulooligosaccharide, fucoidan oligosaccharide, gum arabic oligosaccharide or polyethylene glycol alginic acid oligosaccharide, wherein the oligosaccharide comprises 2 to 20 monosaccharides polymerized.

2. A method for cultivating a plant, which comprises applying a plant growth accelerating oligosaccharide to a seed to coat the seed with the plant growth accelerating oligosaccharide at a ratio of from 5$\gamma$ to 100$\gamma$ per grain of the seed, and then planting the seed and cultivating the plant therefrom, wherein the oligosaccharide is alginic acid oligosaccharide, inulooligosaccharide, fucoidan oligosaccharide, gum arabic oligosaccharide or polyethylene glycol alginic acid oligosaccharide wherein the oligosaccharide comprises 2 to 20 monosaccharides polymerized.

3. A method for cultivating a plant, which comprises applying to the surface of leaves of a plant an aqueous solution of from 20 $\tau$/ml to 200 $\tau$/ml of a plant growth accelerating oligosaccharide and thereafter cultivating said plant, wherein the plant growth accelerating oligosaccharide is alginic acid oligosaccharide, inulooligosaccharide, fucoidan oligosaccharide, gum arabic oligosaccharide or polyethylene glycol alginic acid oligosaccharide, wherein the oligosaccharide comprises 2 to 20 monosaccharides polymerized.

4. A method for cultivating a plant, which comprises applying into the soil an aqueous solution of from 30 $\tau$/ml to 350 $\tau$/ml of a plant growth accelerating oligosaccharide at a ratio of from 0.5 kg to 5.0 kg per hectare and thereafter cultivating the plant, wherein the plant growth accelerating oligosaccharide is alginic acid oligosaccharide, inulooligosaccharide, fucoidan oligosaccharide, gum arabic oligosaccharide or polyethylene glycol alginic acid oligosaccharide, wherein the oligosaccharide comprises 2 to 20 monosaccharides polymerized.

5. A method for cultivating a plant, which comprises mixing a plant growth accelerating oligosaccharide with a liquid fertilizer for hydroponics, at a concentration of from 2.5 $\tau$/ml to 250 $\tau$/ml and thereafter cultivating said plant in the aqueous medium comprising said liquid fertilizer for hydroponics, wherein the plant growth accelerating oligosaccharide is alginic acid oligosaccharide, inulooligosaccharide, fucoidan oligosaccharide, gum arabic oligosaccharide or polyethylene glycol alginic acid oligosaccharide, wherein the oligosaccharide comprises 2 to 20 monosaccharides polymerized.

6. A method for cultivating a plant, which comprises coating a plant growth accelerating oligosaccharide on a fertilizer or mixing said plant growth accelerating oligosaccharide with said fertilizer at a ratio of from 0.1% to 0.5% and thereafter applying the thus treated fertilizer to the soil in the vicinity of the plant, and thereafter cultivating said plant, wherein the plant growth accelerating oligosaccharide is alginic acid oligosaccharide, inulooligosaccharide, fucoidan oligosaccharide, gum arabic oligosaccharide or polyethylene glycol alginic acid oligosaccharide, wherein the oligosaccharide comprises 2 to 20 monosaccharides polymerized.

* * * * *